(12) United States Patent
Echigo et al.

(10) Patent No.: US 8,889,919 B2
(45) Date of Patent: Nov. 18, 2014

(54) CYCLIC COMPOUND, PROCESS FOR PRODUCTION OF THE CYCLIC COMPOUND, RADIATION-SENSITIVE COMPOSITION, AND METHOD FOR FORMATION OF RESIST PATTERN

(75) Inventors: Masatoshi Echigo, Hiratsuka (JP); Hiromi Hayashi, Hiratsuka (JP)

(73) Assignee: Mitsubishi Gas Chemical Company, Inc., Tokyo (JP)

( * ) Notice: Subject to any disclaimer, the term of this patent is extended or adjusted under 35 U.S.C. 154(b) by 0 days.

(21) Appl. No.: 13/392,263

(22) PCT Filed: Aug. 26, 2010

(86) PCT No.: PCT/JP2010/064521
§ 371 (c)(1),
(2), (4) Date: Feb. 24, 2012

(87) PCT Pub. No.: WO2011/024916
PCT Pub. Date: Mar. 3, 2011

(65) Prior Publication Data
US 2012/0171615 A1    Jul. 5, 2012

(30) Foreign Application Priority Data
Aug. 31, 2009   (JP) ................... 2009-200631

(51) Int. Cl.
C07C 43/23   (2006.01)
C07C 41/30   (2006.01)
G03F 7/004   (2006.01)

(52) U.S. Cl.
USPC ........... 568/717; 568/719; 568/720; 560/81; 560/83; 430/270.1; 430/913; 430/927; 430/945

(58) Field of Classification Search
USPC .............................. 525/502, 507; 528/98, 91
See application file for complete search history.

(56) References Cited

U.S. PATENT DOCUMENTS

| 5,218,060 A | 6/1993 | Rolfe et al. |
| 5,439,989 A | 8/1995 | Morton et al. |
| 5,952,145 A | 9/1999 | Yamanaka et al. |
| 2008/0153031 A1 | 6/2008 | Echigo et al. |
| 2010/0047709 A1 | 2/2010 | Echigo et al. |

FOREIGN PATENT DOCUMENTS

| DE | 278139 | 4/1990 |
| DE | 278140 | 4/1990 |
| EP | 0 632 003 | 1/1995 |
| JP | 5-70550 | 3/1993 |
| JP | 6-501971 | 3/1994 |
| JP | 6-282067 | 10/1994 |
| JP | 7-64285 | 3/1995 |
| JP | 8-137138 | 5/1996 |
| JP | 2003306470 A * | 10/2003 |
| JP | 2004-262822 | 9/2004 |
| JP | 2005-326838 | 11/2005 |
| JP | 2006-248979 | 9/2006 |
| JP | 2007-008875 | 1/2007 |
| JP | 2008-145539 | 6/2008 |
| JP | 2009-173623 | 8/2009 |

OTHER PUBLICATIONS

U.S. Appl. No. 13/392,205 to Masatoshi Echigo et al., which was filed on Feb. 24, 2012.
U.S. Appl. No. 13/392,254 to Masatoshi Echigo et al., which was filed on Feb. 24, 2012.
U.S. Appl. No. 13/393,988 to Hiromi Hayashi et al., which was filed on Mar. 2, 2012.
Placido Neri et al., "Synthesis of Glycidyl Calixarenes, Versatile Substrates for the Preparation of Chiral Calizarene-Based Ligands ", , 1996, pp. 17-20, vol. 7, No. 1.
Shuling Gong et al., "Playing a special role in the monofunctionalization of calixarenes by epoxides", New Journal of Chemistry, 2002, pp. 1827-1830, vol. 26, No. 12.
Hiroto Kudo et al., "New large refractive-index change materials: synthesis and photochemical valence isomerization of the calixarene derivatives containing norbornadiene moieties", Bulletin of the Chemical Society of Japan, 2004, pp. 1415-1422, vol. 77, No. 7.
Search report from International Patent Application No. PCT/JP2010/064521, mail date is Sep. 28, 2010.

* cited by examiner

*Primary Examiner* — Amanda C. Walke
(74) *Attorney, Agent, or Firm* — Greenblum & Bernstein, P.L.C.

(57) ABSTRACT

A cyclic compound represented by formula (1):

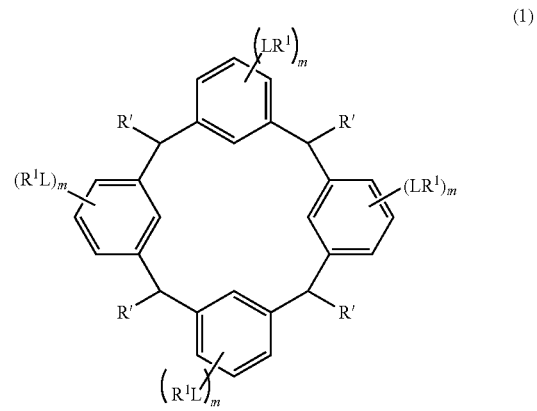

wherein L, $R^1$, R', and m are as defined in the specification. The cyclic compound of formula (1) is highly soluble to a safety solvent, highly sensitive, and capable of forming resist patterns with good profile. Therefore, the cyclic compound is useful as a component of a radiation-sensitive composition.

20 Claims, No Drawings

CYCLIC COMPOUND, PROCESS FOR PRODUCTION OF THE CYCLIC COMPOUND, RADIATION-SENSITIVE COMPOSITION, AND METHOD FOR FORMATION OF RESIST PATTERN

TECHNICAL FIELD

The present invention relates to a cyclic compound represented by a specific chemical formula which is useful as an acid-amplified, non-polymeric resist material, a radiation-sensitive composition comprising the cyclic compound, and a method of forming a resist pattern using the composition.

BACKGROUND ART

Conventionally known resist materials are generally polymeric materials capable of forming amorphous thin film. For example, a solution of a polymeric resist material, such as polymethyl methacrylate, polyhydroxystyrene having an acid-dissociating group and polyalkyl methacrylate, is applied on a substrate to form a thin resist film, which is then irradiated with ultraviolet ray, far ultraviolet ray, electron beam, extreme ultraviolet ray (EUV), X-ray, etc., to form line patterns having a line width of about 45 to 100 nm.

The polymeric resists generally have a molecular weight as large as about 10,000 to 100,000 and a broad molecular weight distribution. Therefore, in a lithographic fine process using the polymeric resist, the surface of the fine patterns is roughened, thereby making it difficult to control the dimension of patterns and reducing the product yield. Thus, the conventional lithographic techniques using the known polymeric resist materials have limitations in fine processing. To produce finer patterns, various low-molecular resist materials have been proposed.

For example, Patent Documents 1 and 2 propose alkali-developable negative-type radiation-sensitive compositions mainly comprising a low-molecular, polynuclear polyphenol compound. However, the profile of the obtained resist pattern is poor because of insufficient heat resistance.

As other low-molecular resist materials, Patent Document 1 and Non-Patent Document 1 propose alkali-developable negative-type radiation-sensitive compositions mainly comprising a low-molecular cyclic polyphenol compound. The proposed low-molecular cyclic polyphenol compounds have been expected to provide resist patterns with high resolution and small roughness because of their small molecular size. Since the low-molecular cyclic polyphenol compound has a rigid cyclic structure, it exhibits a high heat resistance, considering its low molecular weight.

However, the low-molecular cyclic polyphenol compound now available is less soluble in a safety solvent used in the semiconductor production process, low in the sensitivity, and provides a resist pattern with a poor profile. Therefore, the improvement of the low-molecular cyclic polyphenol compound has been demanded.

Patent Document 1: JP 2005-326838A
Patent Document 2: JP 2008-145539A
Patent Document 3: JP 2009-173623A
Non-Patent Document 1: T. Nakayama, M. Nomura, K. Haga, M. Ueda: Bull. Chem. Soc. Jpn., 71, 2979 (1998)

DISCLOSURE OF THE INVENTION

An object of the invention is to provide a cyclic compound which is highly soluble in a safety solvent, highly sensitive, and capable of providing a resist pattern with good profile, a production method thereof, a radiation-sensitive composition comprising the cyclic compound, and a method of forming a resist pattern using the radiation-sensitive composition.

As a result of extensive research, the inventors have found that a cyclic compound having a specific structure is highly soluble in a safety solvent, highly sensitive, and capable of providing a resist pattern with good profile. The invention is based on this finding.

The invention relates to:

1. A cyclic compound represented by formula (1):

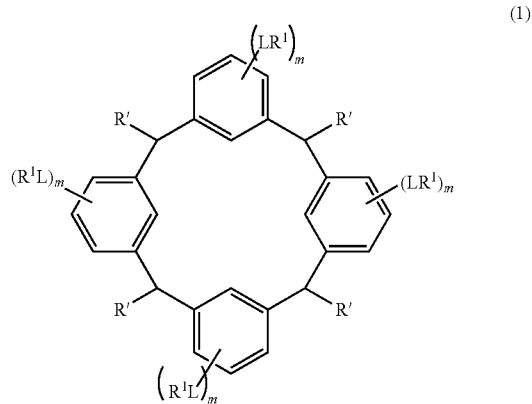

(1)

wherein each L is independently a single bond or a divalent organic group selected from the group consisting of a linear or branched alkylene group having 1 to 20 carbon atoms, a cycloalkylene group having 3 to 20 carbon atoms, an arylene group having 6 to 24 carbon atoms, —O—, —OC(=O)—, —OC(=O)O—, —N($R^5$)—C(=O)— wherein $R^5$ is hydrogen or an alkyl group having 1 to 10 carbon atoms, —N($R^5$)—C(=O)O— wherein $R^5$ is as defined above, —S—, —SO—, —$SO_2$—, and a combination of any of preceding groups;

each $R^1$ is independently an alkyl group having 1 to 20 carbon atoms, a cycloalkyl group having 3 to 20 carbon atoms, an aryl group having 6 to 20 carbon atoms, an alkoxyl group having 1 to 20 carbon atoms, cyano group, nitro group, hydroxyl group, a heterocyclic group, a halogen, carboxyl group, glycidyl group, an alkylsilyl group having 1 to 20 carbon atoms, or hydrogen atom, with the proviso that at least one of $R^1$ is glycidyl group and another at least one of $R^1$ is hydrogen atom;

each R' is independently an alkyl group having 2 to 20 carbon atoms or an aryl group represented by the following formula:

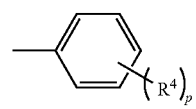

wherein $R^4$ is an alkyl group having 1 to 20 carbon atoms, a cycloalkyl group having 3 to 20 carbon atoms, an aryl group having 6 to 20 carbon atoms, an alkoxy group having 1 to 20 carbon atoms, cyano group, nitro group, an heterocyclic group, a halogen, carboxyl group, hydroxyl group, glycidyl group, or an alkylsilyl group having 1 to 20 carbon atoms, and p is an integer of 0 to 5; and m is an integer of 1 to 4.

2. The cyclic compound of item 1 represented by formula (2):

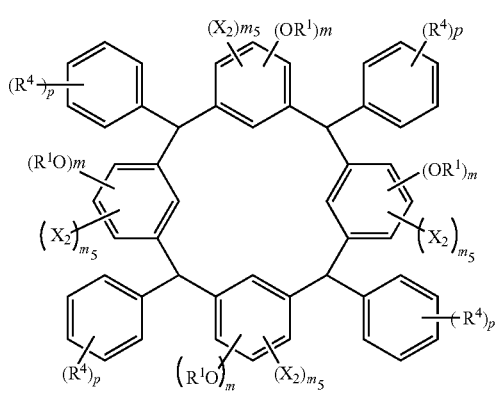

(2)

wherein $R^1$, $R^4$, p, and m are as defined above, $X_2$ is a hydrogen or halogen atom, $m_5$ is an integer of 0 to 3, and $m+m_5=4$.

3. The cyclic compound of item 1 or 2, having a molecular weight of 800 to 5000.

4. A method of producing the cyclic compound of any one of items 1 to 3, which comprises a step of subjecting at least one aldehyde compound (A1) and at least one phenol compound (A2) to condensation reaction, to obtain a cyclic compound (A) and a step of subjecting the cyclic compound (A) and at least one epihalohydrin (A3) to dehydrohalogenation reaction.

5. The method of item 4, wherein the aldehyde compound (A1) has 1 to 4 formyl groups and 2 to 59 carbon atoms, and the phenol compound (A2) has 1 to 3 phenolic hydroxyl groups and 6 to 15 carbon atoms.

6. The method of item 4 or 5, wherein the cyclic compound (A) has a molecular weight of 700 to 5000.

7. The method of any one of items 4 to 6, wherein by the dehydrohalogenation between the cyclic compound (A) and the at least one epihalohydrin (A3), at least one phenolic hydroxyl group of the cyclic compound (A) is converted to glycidyloxy group while maintaining another at least one phenolic hydroxyl group unchanged.

8. A radiation-sensitive composition comprising the cyclic compound of any one of items 1 to 3 and a solvent.

9. The radiation-sensitive composition of item 8, comprising 1 to 80% by weight of a solid component and 20 to 99% by weight of a solvent.

10. The radiation-sensitive composition of item 8 or 9, wherein a content of the cyclic compound is 50 to 99.999% by weight of a total weight of the solid component.

11. The radiation-sensitive composition of any one of items 8 to 10, further comprising an acid generator (C) which directly or indirectly generates acid upon exposure to any radiation selected from the group consisting of visible light, ultraviolet ray, excimer laser, electron beam, extreme ultraviolet ray (EUV), X-ray, and ion beam.

12. The radiation-sensitive composition of any one of items 8 to 11, further comprising an acid crosslinking agent (G).

13. The radiation-sensitive composition of any one of items 8 to 12, further comprising an acid-diffusion controller (E).

14. The radiation-sensitive composition of any one of items 8 to 13, wherein the cyclic compound is represented by formula (2):

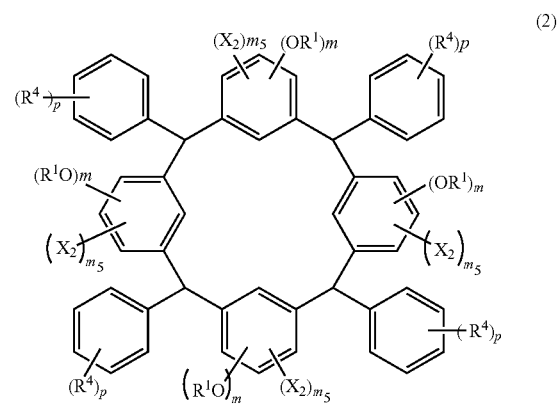

(2)

wherein $R^1$, $R^4$, p, and m are as defined above, $X_2$ is a hydrogen or halogen atom, $m_5$ is an integer of 0 to 3, and $m+m_5=4$.

15. The radiation-sensitive composition of any one of items 8 to 14, wherein the cyclic compound is selected from the group consisting of compounds represented by formulae (6-5) to (6-8):

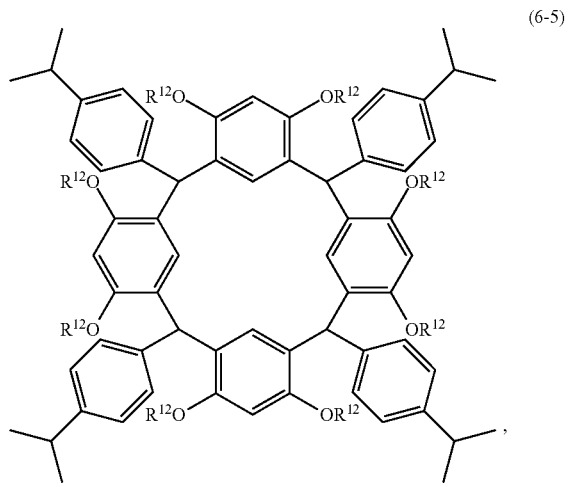

(6-5)

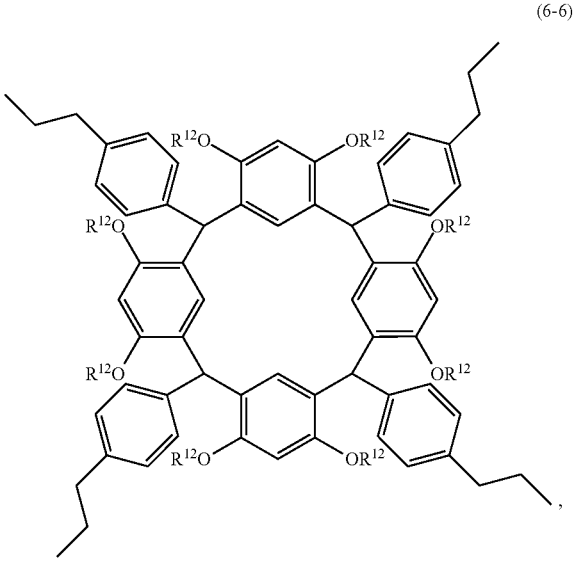

(6-6)

-continued (6-7)

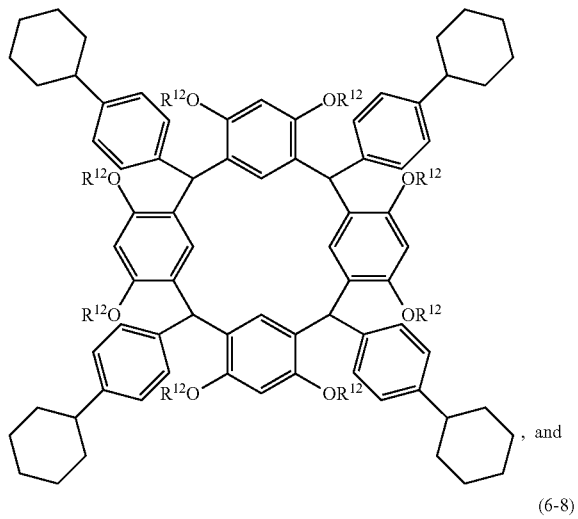
, and (6-8)

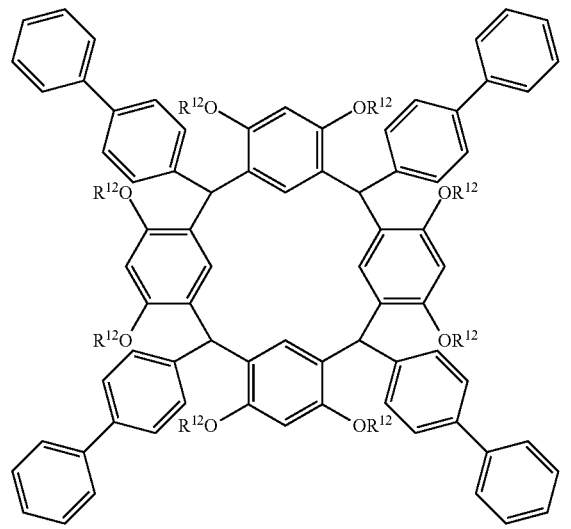

wherein $R^{12}$ is glycidyl group or hydrogen atom, with the proviso that at least one $R^{12}$ is glycidyl group and another at least one of $R^{12}$ is hydrogen atom.

16. The radiation-sensitive composition of any one of items 8 to 15, wherein the solid component comprises 50 to 99.4% by weight of the cyclic compound, 0.001 to 49% by weight of the acid generator (C), 0.5 to 49% by weight of the acid crosslinking agent (G), 0.001 to 49% by weight of the acid-diffusion controller (E), and 0 to 49% by weight an optional component (F), each based on the solid component.
17. The radiation-sensitive composition of any one of items 8 to 16, capable of forming an amorphous film by spin coating.
18. The radiation-sensitive composition of any one of items 8 to 17, wherein a dissolving speed of the amorphous film into a 2.38% by weight aqueous solution of tetramethylammonium hydroxide at 23° C. is 10 Å/s or more.
19. The radiation-sensitive composition of item 18, wherein a dissolving speed of the amorphous film into a 2.38% by weight aqueous solution of tetramethylammonium hydroxide at 23° C. is 5 Å/s or less after exposed to KrF excimer laser, extreme ultraviolet ray, electron beam, or X-ray or after heated at 20 to 250° C.
20. A method of forming resist pattern, which comprises a step of coating the radiation-sensitive composition of any one of items 8 to 19 on a substrate, thereby forming a resist film; a step of exposing the resist film to radiation; and a step of developing the exposed resist film.

According to the invention, a cyclic compound which is highly soluble in a safety solvent, highly sensitive, and capable of providing a resist pattern with good profile, a production method thereof, a radiation-sensitive composition comprising the cyclic compound, and a method of forming a resist pattern using the radiation-sensitive composition are provided.

BEST MODE FOR CARRYING OUT THE INVENTION

The invention will be described below in detail.
Cyclic Compound and Production Method Thereof
The invention relates to a cyclic compound useful as a resist material and the production method thereof.
The cyclic compound of the invention is represented by formula (1);

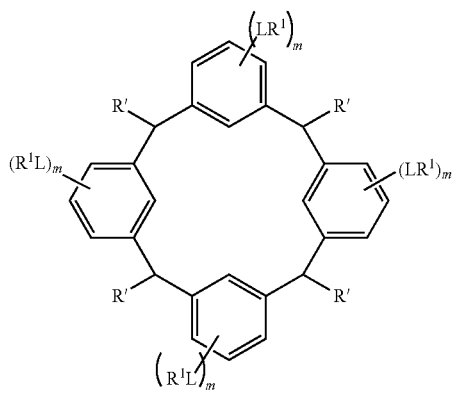

(1)

In formula (1), each L is independently a single bond or a divalent organic group selected from the group consisting of a linear or branched alkylene group having 1 to 20 carbon atoms (preferably, methylene, ethylene, propylene, butylene, pentylene, hexylene, methylmethylene, methylethylene, dimethylmethylene, and methylethylene), a cycloalkylene group having 3 to 20 carbon atoms (preferably, cyclopropylene, cyclobutylene, cyclopentylene, or cyclohexylene), an arylene group having 6 to 24 carbon atoms (preferably, phenylene, naphthylene, anthranylene, or phenanthrylene), —O—, —OC(=O)—, —OC(=O)O—, —N($R^5$)—C(=O)—, —N($R^5$)—C(=O)O—, —S—, —SO—, —$SO_2$—, and a combination of any of the preceding groups. $R^5$ is hydrogen or an alkyl group having 1 to 10 carbon atoms (preferably, methyl, ethyl, propyl, isopropyl, butyl, isobutyl, or t-butyl).

Each $R^1$ is independently an alkyl group having 1 to 20 carbon atoms (preferably, methyl, ethyl, propyl, isopropyl, butyl, isobutyl, or t-butyl), a cycloalkyl group having 3 to 20 carbon atoms (preferably, cyclopropyl, cyclobutyl, cyclopentyl, or cyclohexyl), an aryl group having 6 to 20 carbon atoms (preferably, phenyl, naphthyl, anthranyl, or phenanthryl), an alkoxyl group having 1 to 20 carbon atoms (preferably, methoxy, ethoxy, propoxy, isopropoxy, butoxy, isobutoxy, or t-butoxy), cyano group, nitro group, hydroxyl group, a heterocyclic group (preferably, pyridyl group, furyl group, thienyl group, oxazolyl group, thiazolyl group, isoxazolyl group, isothiazolyl group, pyrazolyl group, benzofuranyl group, or morpholinyl group), a halogen (preferably, fluorine, chlorine, bromine, or iodine), carboxyl group, glycidyl group, and an alkylsilyl group having 1 to 20 carbon atoms (preferably, trimethylsilyl, triethylsilyl, tripropylsilyl, dimethylsilyl, diethylsilyl, dipropylsilyl, methylsilyl, ethylsilyl, or propylsilyl), or hydrogen atom, with the proviso that at least one $R^1$ is glycidyl group and another at least one of $R^1$ is hydrogen atom.

R' is independently an alkyl group having 2 to 20 carbon atoms (preferably, methyl, ethyl, propyl, isopropyl, butyl, isobutyl, t-butyl, pentyl, isopentyl, neopentyl, hexyl, octyl, decyl, dodecyl, or undecyl), or an aryl group represented by the following formula:

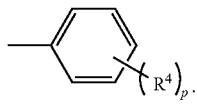

In the above formula, $R^4$ is an alkyl group having 1 to 20 carbon atoms (preferably, methyl, ethyl, propyl, isopropyl, butyl, isobutyl, or t-butyl), a cycloalkyl group having 3 to 20 carbon atoms (preferably, cyclopropyl, cyclobutyl, cyclopentyl, or cyclohexyl), an aryl group having 6 to 20 carbon atoms (preferably, phenyl, naphthyl, anthranyl, or phenanthryl), an alkoxy group having 1 to 20 carbon atoms (preferably, methoxy, ethoxy, propoxy, isopropoxy, butoxy, isobutoxy, or t-butoxy), cyano group, nitro group, a heterocyclic group (preferably, pyridyl group, furyl group, thienyl group, oxazolyl group, thiazolyl group, isoxazolyl group, isothiazolyl group, pyrazolyl group, benzofuranyl group, or morpholinyl group), a halogen (preferably, fluorine, chlorine, bromine, or iodine), carboxyl group, hydroxyl group, glycidyl group, or an alkylsilyl group having 1 to 20 carbon atoms (preferably, trimethylsilyl, triethylsilyl, tripropylsilyl, dimethylsilyl, diethylsilyl, dipropylsilyl, methylsilyl, ethylsilyl, or propylsilyl). The subscript p is an integer of 0 to 5.

The subscript m is an integer of 1 to 4. The $-LR^1$ groups on the different benzene rings may be the same or different. When m is an integer of 2 to 4, $-LR^1$ groups on the same benzene ring may be the same or different.

The cyclic compound represented by formula (1) is preferably represented by any of formulae (2) to (7):

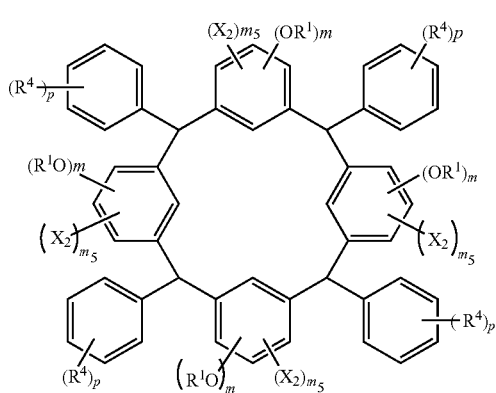

(2)

wherein $R^1$, $R^4$, p, and m are the same as defined above, $X_2$ is a hydrogen or halogen atom (preferably, fluorine, chlorine, bromine, or iodine), $m_5$ is an integer of 0 to 3, and $m+m_5=4$;

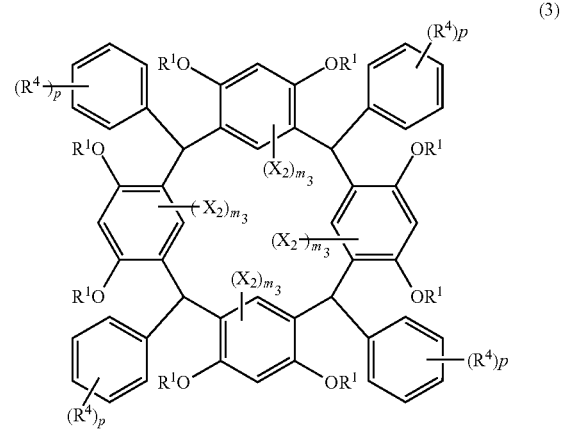

(3)

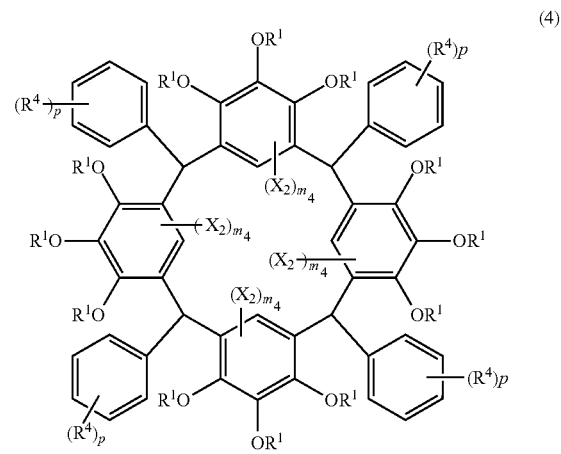

(4)

wherein $R^1$, $R^4$, $X_2$, and p are the same as defined above, $m_3$ is an integer of 1 to 2, and $m_4$ is 1;

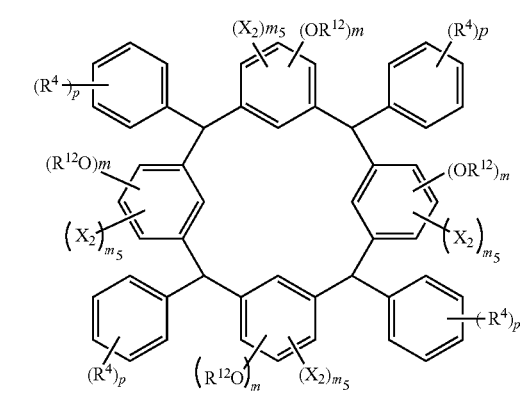

(5)

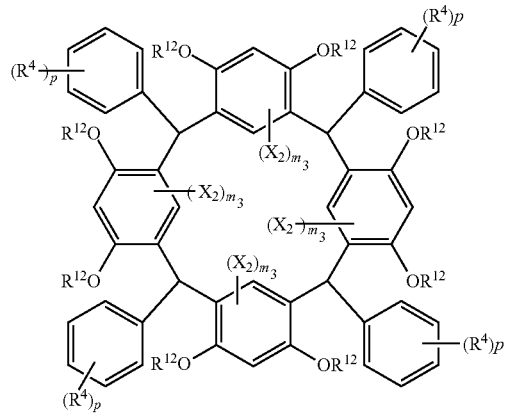

(6)

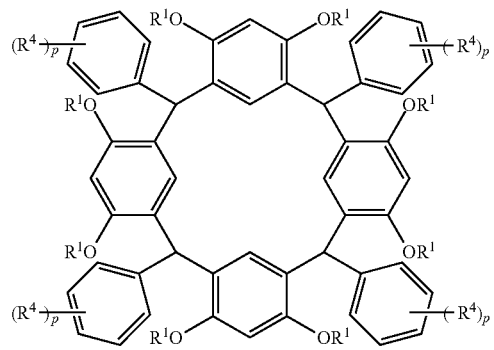

(5-2)

wherein R¹, R⁴, and p are as defined above,

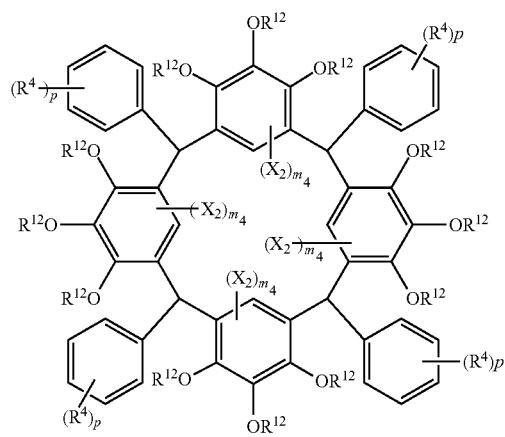

(7)

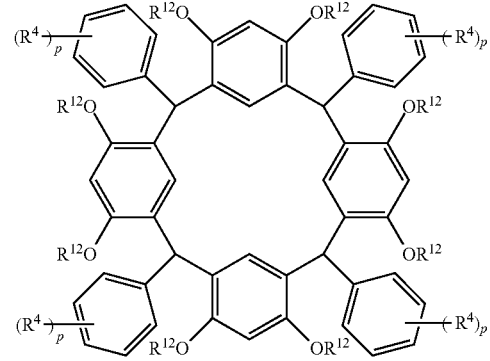

(5-3)

wherein R¹², R⁴, p are as defined above.

The cyclic compound is still more preferably selected from the group consisting of the compounds represented by formulae (6-1) to (6-8):

wherein $R^4$, $X_2$, p, m, $m_3$, $m_4$, and $m_5$ are the same as defined above, and $R^{12}$ is glycidyl group or hydrogen atom, with the proviso that at least one $R^{12}$ is glycidyl group and another at least one of $R^{12}$ is hydrogen atom.

The cyclic compound of the invention is excellent in film-forming properties because of its high heat resistance and amorphous properties, not sublimable, and excellent in alkali developability and etching resistance. Therefore, the cyclic compound is useful as a resist material, particularly as a main component (base material) of a resist material.

In addition, the cyclic compound can be produced in high yields from the industrially available raw materials, for example, by the dehydrating condensation reaction of various aldehydes, such as aromatic aldehyde, and phenols, such as resorcinol and pyrogallol, in the presence of a non-metallic catalyst, such as hydrochloric acid, and then subjecting the obtained precursor for the cyclic compound and an epihalohydrin to dehydrohalogenation reaction. Therefore, the cyclic compound is of great practical value.

The cyclic compound is more preferably selected from the group consisting of the compounds represented by formulae (5-2) and (5-3):

(6-1)

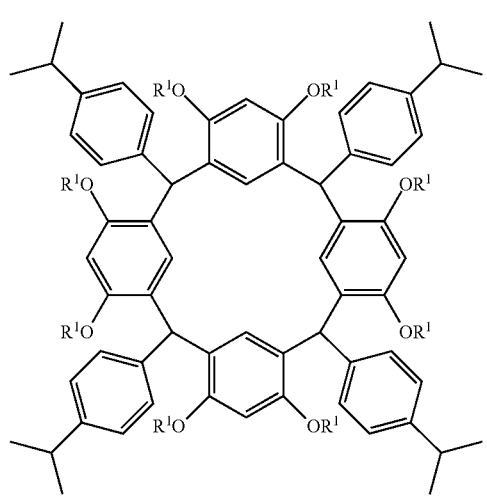

-continued
(6-2)
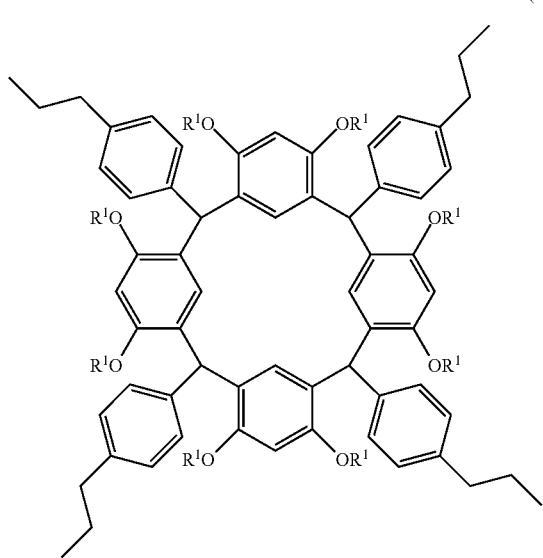
wherein R¹ is as defined above,
(6-3)
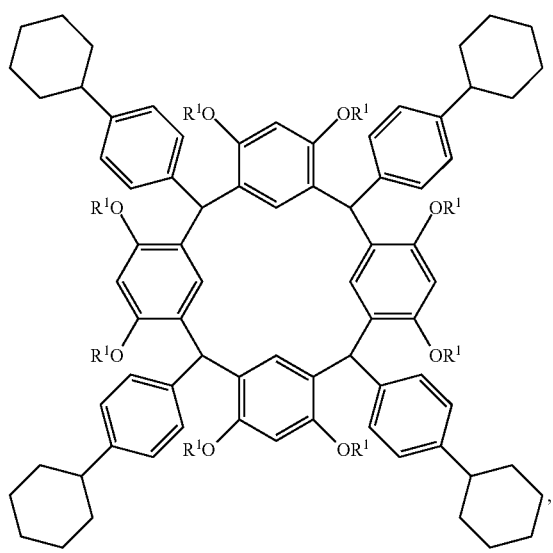
(6-4)
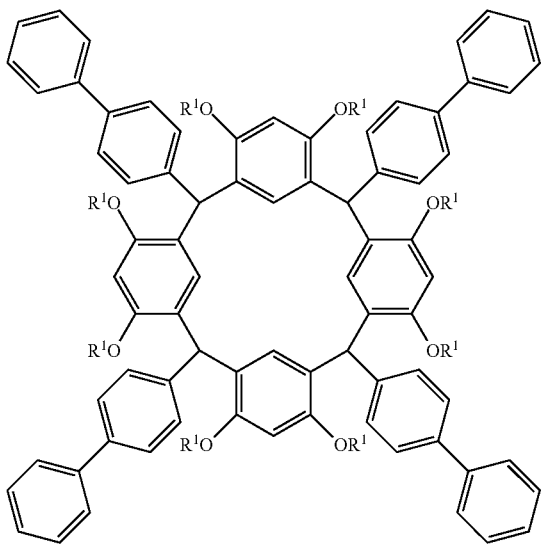
wherein R¹ is as defined above,
(6-5)
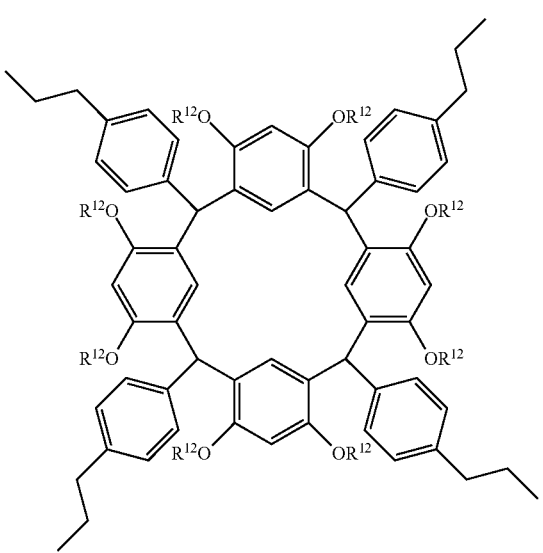
(6-6)

wherein R¹² is as defined above,

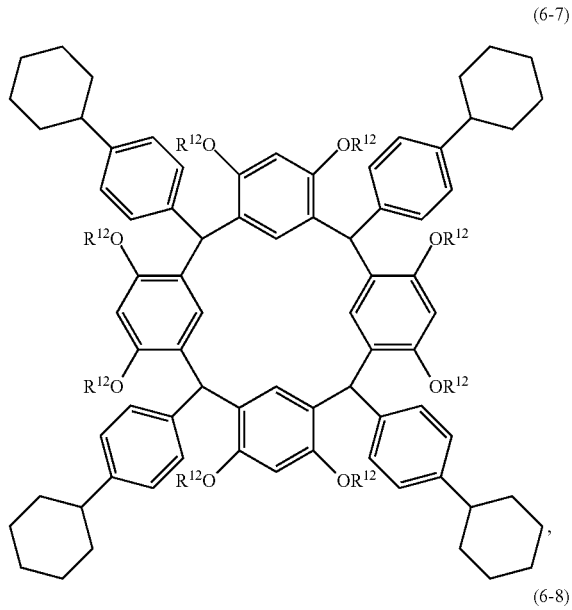

(6-7)

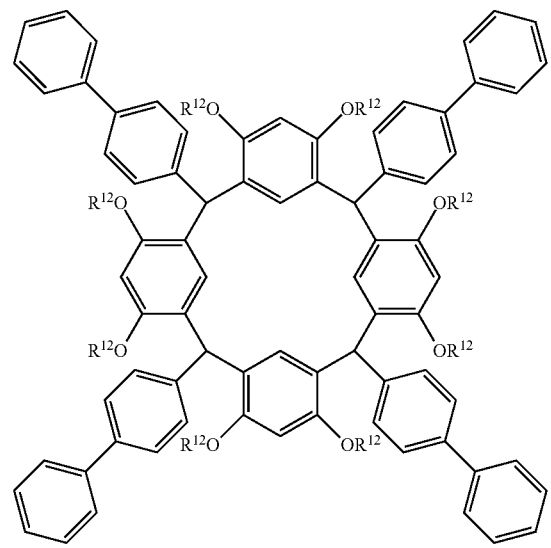

(6-8)

wherein R¹² is as defined above.

Of the compounds represented by formulae (6-1) to (6-8), the cyclic compound selected from the compounds represented by formula (6-7) is particularly preferred, because the solubility to safety solvent is high, the sensitivity is high, and the resist pattern with good profile is formed.

The molecular weight of the cyclic compound represented by formula (1) is 800 to 5000, preferably 800 to 2000, and more preferably 1000 to 2000. Within the above ranges, the resolution is improved, while maintaining the film-forming property necessary for the resist.

The cyclic compound may be cis-isomer, trans-isomer, or a mixture thereof. One pure isomer is preferably used when the cyclic compound is used as a resist component of the radiation-sensitive composition, because a resist film with high uniformity is obtained. One pure isomer of the cyclic compound is obtained by a known method, for example, the separation using column chromatography or preparative liquid chromatography or the optimization of the reaction conditions for the production thereof, such as solvent and temperature.

The cyclic compound of formula (1) is produced by subjecting at least one aldehyde compound (A1) and at least one phenol compound (A2) to condensation reaction, thereby obtaining the precursor (cyclic compound (A)) of the cyclic compound, and then, the precursor of the cyclic compound and at least one epihalohydrin (A3) to dehydrohalogenation reaction.

The cyclic compound of formula (1) is produced preferably by subjecting at least one aromatic aldehyde compound (A1A) and at least one phenol compound (A2) to condensation reaction, and then, subjecting the resulting cyclic compound (A) and at least one epihalohydrin (A3) to dehydrohalogenation reaction.

Alternatively, the cyclic compound of formula (1) may be produced by subjecting at least one phenol compound (A2) and at least one epihalohydrin (A3) to dehydrohalogenation reaction, and then, subjecting the resulting phenol compound (A2A) and at least one aldehyde compound (A1) to condensation reaction. In this production method, at least one phenolic hydroxyl group of the phenol compound (A2A) must remain unchanged. However, since it is difficult to so control the reaction conditions, the yield of the cyclic compound is low. Thus, this method is not so suitable.

The aldehyde compound (A1) has 3 to 59 carbon atoms and 1 to 4 formyl groups and is selected from the aromatic aldehyde compound (A1A) and the aliphatic aldehyde compound (A1B). The aromatic aldehyde compound (A1A) is preferably a benzaldehyde compound having 7 to 24 carbon atoms, for example, benzaldehyde, methylbenzaldehyde, dimethylbenzaldehyde, ethylbenzaldehyde, propylbenzaldehyde, butylbenzaldehyde, ethylmethylbenzaldehyde, isopropylmethylbenzaldehyde, diethylbenzaldehyde, anisaldehyde, naphthaldehyde, anthraldehyde, cyclopropylbenzaldehyde, cyclobutylbenzaldehyde, cyclopentylbenzaldehyde, cyclohexylbenzaldehyde, phenylbenzaldehyde, naphthylbenzaldehyde, adamantylbenzaldehyde, norbornylbenzaldehyde, lactylbenzaldehyde, isopropylbenzaldehyde, normalpropylbenzaldehyde, bromobenzaldehyde, dimethylaminobenzaldehyde, hydroxybenzaldehyde, dihydroxybenzaldehyde, and trihydroxybenzaldehyde, with isopropylbenzaldehyde, normalpropylbenzaldehyde, cyclohexylbenzaldehyde, and phenylbenzaldehyde being preferred, and cyclohexylbenzaldehyde and 4-isopropylbenzaldehyde being more preferred. The aromatic aldehyde compound (A1A) may have a linear or branched alkyl group having 1 to 4 carbon atoms, cyano group, hydroxyl group, or halogen as long as the effect of the invention is not adversely affected. The aromatic aldehyde compound (A1A) may be used alone or in combination of two or more.

The aliphatic aldehyde compound (A1B) is preferably a compound having 3 to 24 carbon atoms, for example, propanal, isopropanal, butanal, isobutanal, t-butanal, pentanal, isopentanal, neopentanal, hexanal, isohexanal, octanal, decanal, dodecanal, undecenal, cyclopropanecarboxaldehyde, cyclobutanecarboxaldehyde, and cyclohexanecarboxaldehyde, with isobutanal, t-butanal, pentanal, isopentanal, neopentanal, hexanal, isohexanal, octanal, decanal, dodecanal, cyclopropanecarboxaldehyde, cyclobutanecarboxaldehyde, and cyclohexanecarboxaldehyde being preferred, and octanal, decanal, dodecanal, and cyclohexanecarboxaldehyde being more preferred. The aliphatic aldehyde compound (A1B) may have cyano group, hydroxyl group, or halogen as long as the effect of the invention is not adversely affected.

The aliphatic aldehyde compound (A1B) may be used alone or in combination of two or more.

The phenol compound (A2) has preferably 6 to 15 carbon atoms and 1 to 3 phenolic hydroxyl groups. Examples thereof include phenol, catechol, resorcinol, hydroquinone, and pyrogallol, with resorcinol and pyrogallol being preferred, and resorcinol being more preferred. The phenol compound (A2) may have a linear or branched alkyl group having 1 to 4 carbon atoms, cyano group, hydroxyl group, or halogen as long as the effect of the invention is not adversely affected. The phenol compound (A2) may be used alone or in combination of two or more.

Examples of the epihalohydrin (A3) include epichlorohydrin and epibromohydrin, with epichlorohydrin being preferred. The epihalohydrin (A3) may have a linear or branched alkyl group having 1 to 4 carbon atoms, cyano group, hydroxyl group, or halogen as long as the effect of the invention is not adversely affected. The epihalohydrin (A3) may be used alone or in combination of two or more.

The cyclic compound represented by formula (1) is produced by a known method. For example, one mole of the aldehyde compound (A1) and 0.1 to 10 mol of the phenol compound (A2) are allowed to react at 60 to 150° C. for 0.5 to 20 h in an organic solvent, such as methanol and ethanol, in the presence of an acid catalyst (hydrochloric acid, sulfuric acid, p-toluenesulfonic acid, etc.). Thereafter, by filtration, washing with an alcohol, such as methanol, washing with water, separation by filtration, and drying, the cyclic compound (A) preferably having a molecular weight of 700 to 5000 is obtained. Alternatively, the cyclic compound (A) is produced by a similar reaction using a basic catalyst (sodium hydroxide, barium hydroxide, 1,8-diazabicyclo[5.4.0]undecene-7, etc.). Further, the cyclic compound (A) is produced by converting the aldehyde compound (A1) to a dihalide by a hydrogen halide or a halogen gas and then allowing the isolated dihalide and the phenol compound (A2) to react.

Then, one mole of the cyclic compound (A) and 0.1 to 10 mol of the epihalohydrin (A3) are allowed to react at 0 to 150° C. for about 0.5 to 20 h in an organic solvent, such as N-methyl-2-pyrrolidone, in the presence of a basic catalyst (triethylamine, ammonia, sodium hydroxide, etc.). By this reaction, at least one phenolic hydroxyl group in the cyclic compound (A) is maintained unchanged, while converting another at least one phenolic hydroxyl group to glycidyloxy group. Then, by filtration, washing with an alcohol, such as methanol, washing with water, separation by filtration, and drying, the cyclic compound represented by formula (1) is obtained.

It is preferred to use two or more kinds of at least one of the aldehyde compound (A1), the phenol compound (A2), and the epihalohydrin (A3), because the solubility of the cyclic compound in the safety solvent is increased.

To reduce the amount of residual metal, the cyclic compound may be purified, if necessary. If the acid catalyst or catalyst aid remains, the storage stability of the radiation-sensitive composition is generally reduced, or the sensitivity of the radiation-sensitive composition is generally lowered if the basic catalyst remains. Therefore, the cyclic compound may be purified to reduce the remaining amount of these catalysts. The purification may be carried out by any of known methods without limitation as long as the cyclic compound is not unfavorably changed, for example, by washing with water, washing with an acidic aqueous solution, washing with a basic aqueous solution, treatment with an ion exchange resin, and silica gel column chromatography. The purification is preferably conducted by combining two or more of these purification methods. An optimum acidic aqueous solution, basic aqueous solution, ion exchange resin or silica gel column can be suitably selected by taking the amount and kind of the metal, acidic compound, and basic compound to be removed and the kind of the cyclic compound to be purified into consideration. For example, hydrochloric acid, an aqueous solution of nitric acid and an aqueous solution of acetic acid, each having a concentration of 0.01 to 10 mol/L, are used as the acidic aqueous solution. An ammonia solution having a concentration of 0.01 to 10 mol/L is used as the basic aqueous solution. A cation exchange resin, such as Amberlyst 15J-HG Dry manufactured by Organo Corporation, is used as the ion exchange resin. The purified product may be dried by a known method, such as, but not limited to, a vacuum drying and a hot-air drying, under the conditions not changing the cyclic compound.

The cyclic compound represented by formula (1) forms an amorphous film by spin coating and is applied to the known process for the production of semiconductor.

The cyclic compound represented by formula (1) is useful as a negative-type resist material because it changes to a compound hardly soluble in an alkali developing solution upon exposure to KrF excimer laser, extreme ultraviolet ray, electron beam, or X-ray. This may be because that the condensation reaction between the cyclic compounds is induced upon exposure to KrF excimer laser, extreme ultraviolet ray, electron beam or X-ray, thereby changing the cyclic compound to a compound hardly soluble in an alkali developing solution. The resist pattern thus formed has a very small LER.

The cyclic compound represented by formula (1) is used as a main component of a negative-type, radiation-sensitive composition. In addition, the cyclic compound is usable as an additive for improving the sensitivity and etching resistance. If used as the additive, the content of the cyclic compound is 1 to 49.999% by weight of the total weight of the solid component in the radiation-sensitive composition.

The glass transition temperature of the cyclic compound of the invention is preferably 100° C. or higher, more preferably 120° C. or higher, still more preferably 140° C. or higher, and particularly preferably 150° C. or higher. Within the above ranges, the cyclic compound has a heat resistance enough to keep the pattern profile during a semiconductor lithography process, and the properties, such as resolution, are improved.

The crystallization heat of the cyclic compound of the invention is preferably less than 20 J/g when measured by the differential scanning calorimetry for determining the glass transition temperature. The value of (crystallization temperature)−(glass transition temperature) is preferably 70° C. or more, more preferably 80° C. or more, still more preferably 100° C. or more, and particularly preferably 130° C. or more. If the crystallization heat is less than 20 J/g or the value of (crystallization temperature)−(glass transition temperature) is within the above ranges, the radiation-sensitive composition is easily formed into an amorphous film by spin coating and the film-forming properties necessary for the resist can be kept for a long term, thereby improving the resolution.

In the present invention, the crystallization heat, the crystallization temperature, and the glass transition temperature are determined by a differential scanning calorimetry using DSC/TA-50WS manufactured by Shimadzu Corporation. A sample of about 10 mg in a non-sealed aluminum vial was heated to the melting point or higher at a temperature rising speed of 20° C./min in nitrogen gas flow (50 mL/min). After rapidly cooling, the sample was again heated to the melting point or higher at a temperature rising speed of 20° C./min in nitrogen gas flow (30 mL/min). After rapidly cooling, the sample was heated to 400° C. at a temperature rising speed of 20° C./min in nitrogen gas flow (30 mL/min). The middle point of the difference in the levels of the stepwise base lines (point where the specific heat reduces to half) was employed as the glass transition temperature (Tg), and the temperature of the endothermic peak appeared thereafter was employed as the crystallization temperature. The crystallization heat was determined as the endothermic heat which was obtained from the area of the region surrounded by the endothermic peak and the base line.

It is preferred that the cyclic compound of the invention has a low sublimation ability under atmospheric pressure at 100° C. or lower, preferably at 120° C. or lower, more preferably at 130° C. or lower, still more preferably at 140° C. or lower, and particularly preferably at 150° C. or lower. The low sublimation ability referred to herein means that the weight loss after a thermogravimetric analysis wherein a sample is kept at predetermined temperature for 10 min is 10% or less, preferably 5% or less, more preferably 3% or less, still more preferably 1% or less, and particularly preferably 0.1% or less. If the sublimation ability is low, the contamination of the exposure apparatus by outgas which generates in the exposing process is prevented. In addition, a fine pattern profile with small LER is obtained.

The cyclic compound of the invention preferably satisfies the requirement of F<3.0 wherein F is (total number of atoms)/(total number of carbon atoms−total number of oxygen atoms), and more preferably F<2.5. By satisfying the above requirements, the dry-etching resistance is improved.

The cyclic compound of the invention dissolves in a solvent at 23° C. preferably in 1% by weight or more, more preferably in 5% by weight or more, and still more preferably in 10% by weight or more when measured in the solvent having the highest dissolving power to the cyclic compound among propylene glycol monomethyl ether acetate (PGMEA), propylene glycol monomethyl ether (PGME), cyclohexanone (CHN), cyclopentanone (CPN), 2-heptanone, anisole, butyl acetate, ethyl propionate, and ethyl lactate. Particularly preferably, the cyclic compound dissolves in 20% by weight or more at 23° C. in the solution having the highest dissolving power to the cyclic compound among PGMEA, PGME, and CHN, and still particularly preferably dissolves in 20% by weight or more at 23° C. in PGMEA. With such solubility, the cyclic compound becomes usable in the process for the actual production of semiconductor.

A halogen atom may be introduced into the cyclic compound of the invention, as long as the effect of the present invention is not adversely affected. The content of the number of the halogen atoms based on the number of the total atoms constituting the cyclic compound is preferably 0.1 to 60%, more preferably 0.1 to 40%, still more preferably 0.1 to 20%, particularly preferably 0.1 to 10%, and most preferably 1 to 5%. Within the above ranges, the film-forming properties can be maintained, while increasing the sensitivity to radiation. In addition, the solubility in the safety solvent can be increased.

A nitrogen atom may be introduced into the cyclic compound of the invention, as long as the effect of the present invention is not adversely affected. The content of the number of the nitrogen atoms based on the number of the total atoms constituting the cyclic compound is preferably 0.1 to 40%, more preferably 0.1 to 20%, still more preferably 0.1 to 10%, and particularly preferably 0.1 to 5%. Within the above ranges, the line edge roughness of the resulting resist pattern can be reduced. The introduced nitrogen atom is preferably secondary or tertiary nitrogen atom, with tertiary nitrogen atom being more preferred.

The cyclic compound of the invention may have a crosslinking group which causes a crosslinking reaction by the irradiation with visible light, ultraviolet ray, excimer laser, electron beam, extreme ultraviolet ray (EUV), X-ray, or ion beam or by the reaction induced by the irradiation, as long as the effect of the present invention is not adversely affected. The crosslinking group is introduced into the cyclic compound, for example, by a reaction with a crosslinking group-introducing agent in the presence of a base catalyst. Examples of the crosslinking group include a carbon-carbon multiple bond, an epoxy group, an azide group, a halophenyl group, and chloromethyl group. Examples of the crosslinking group-introducing agent include an acid, an acid halide, an acid anhydride, a derivative of carboxylic acid, such as dicarbonate, and an alkyl halide, each having the crosslinking group. A radiation-sensitive composition containing the cyclic compound having a crosslinking group is also effective as a solvent-soluble, non-polymeric radiation-sensitive composition with high resolution and high heat resistance.

An acid-non-dissociating functional group may be introduced into at least one phenolic hydroxyl group of the cyclic compound of the invention, as long as the effect of the present invention is not adversely affected. The acid-non-dissociating functional group is a characteristic group which is not dissociated in the presence of acid, thereby failing to generate an alkali-soluble group. Examples thereof include a group which is not dissociated by the action of acid, such as a $C_{1-20}$ alkyl group, a $C_{3-20}$ cycloalkyl group, a $C_{6-20}$ aryl group, a $C_{1-20}$ alkoxyl group, cyano group, nitro group, hydroxyl group, a heterocyclic group, a halogen atom, carboxyl group, a $C_{1-20}$ alkylsilyl group, and functional groups derived from derivatives of the preceding groups.

A naphthoquinonediazido ester group may be introduced into at least one phenolic hydroxyl group of the cyclic compound of the invention, as long as the effect of the present invention is not adversely affected. The cyclic compound having at least one phenolic hydroxyl group into which the naphthoquinonediazido ester group is introduce may be used as the main component of a negative-type radiation-sensitive composition, the main component of a positive-type radiation-sensitive composition, and the acid generator or additive for the radiation-sensitive composition.

An acid-generating functional group which generates an acid upon the irradiation with radiation may be introduced into at least one phenolic hydroxyl group of the cyclic compound of the invention, as long as the effect of the present invention is not adversely affected. The cyclic compound obtained by introducing the acid-generating functional group into at least one phenolic hydroxyl group of the cyclic compound may be used as the main component of a negative-type radiation-sensitive composition, the main component of a positive-type radiation-sensitive composition, and the acid generator or additive for the radiation-sensitive composition.

Radiation-Sensitive Composition

The present invention also relates to a radiation-sensitive composition comprising the cyclic compound represented by formula (1) and a solvent. The radiation-sensitive composition preferably comprises 1 to 80% by weight of the solid component and 20 to 99% by weight of the solvent, and the content of the cyclic compound is preferably 50 to 99.999% by weight of the total weight of the solid component.

The radiation-sensitive composition of the invention forms an amorphous film by spin coating. The dissolving speed of the amorphous film in a 2.38 mass % aqueous solution of TMAH at 23° C. is preferably 10 Å/sec or more, more preferably 10 to 10000 Å/sec, and still more preferably 100 to 1000 Å/sec. If being 10 Å/sec or more, the amorphous film dissolves in an alkali developing solution to form a resist pattern. If being 10000 Å/sec or less, the resolution may be improved in some cases. This may be because that the contrast at the interface between the non-exposed portion soluble in an alkali developing solution and the exposed portion insoluble in an alkali developing solution is enhanced by the change of solubility before and after exposing the cyclic compound to radiation. In addition, LER and defects are reduced.

After exposing an amorphous film formed by spin-coating the radiation-sensitive composition of the invention to radiation, such as KrF excimer laser, extreme ultraviolet ray, electron beam and X-ray, the dissolving speed of the exposed area in a 2.38 mass % aqueous solution of TMAH at 23° C. is preferably 5 Å/sec or less, more preferably 0.05 to 5 Å/sec, and still more preferably 0.0005 to 5 Å/sec. If being 5 Å/sec or less, the exposed area is insoluble in an alkali developing solution to form a resist pattern. If being 0.0005 Å/sec or more, the resolution may be improved in some cases. This may be because that the micro surface of the cyclic compound is dissolved to reduce LER. In addition, defects are reduced.

The radiation-sensitive composition of the invention comprises preferably 1 to 80% by weight of the solid component and 20 to 99% by weight of the solvent; more preferably 1 to 50% by weight of the solid component and 50 to 99% by weight of the solvent; still more preferably 2 to 40% by weight of the solid component and 60 to 98% by weight of the solvent; and particularly preferably 2 to 10% by weight of the solid component and 90 to 98% by weight of the solvent.

The content of the cyclic compound represented by formula (1) is preferably 50 to 99.4% by weight, more preferably 55 to 90% by weight, still more preferably 60 to 80% by weight, and particularly preferably 60 to 70% by weight based on the total weight of the solid component (total of the cyclic compound, the acid generator (C), the acid crosslinking agent (G), the acid-diffusion controller (E), and optional component, such as other components (F), the same applies below). Within the above ranges, high resolution is obtained and the line edge roughness is reduced.

The compound of the invention preferably contains at least one acid generator (C) which directly or indirectly generates an acid upon the exposure to the radiation selected from visible light, ultraviolet ray, excimer laser, electron beam, extreme ultraviolet ray (EUV), X-ray, and ion beam. The amount of the acid generator (C) is preferably 0.001 to 49% by weight, more preferably 1 to 40% by weight, still more preferably 3 to 30% by weight and particularly preferably 10 to 25% by weight, each based on the total amount of the solid component. Within the above ranges, a pattern profile with high sensitivity and low edge roughness is obtained. The method of generating the acid is not limited as long as the acid is generated in the system. The use of excimer laser in place of ultraviolet ray, such as g-ray and i-ray, enables a finer processing. If high-energy ray, such as electron beam, extreme ultraviolet ray, X-ray and ion beam, is used, the resist composition can be still more finely processed.

The acid generator (C) is preferably at least one compound selected from the group consisting of the compounds represented by formulae (7-1) to (7-8).

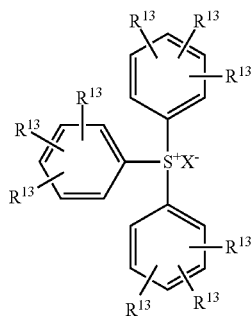

(7-1)

wherein $R^{13}$ groups may be the same or different and each independently a hydrogen atom, a linear, branched, or cyclic alkyl group, a linear, branched, or cyclic alkoxy group, a hydroxyl group, or a halogen atom, $X^-$ is a halide ion or a sulfonate ion having an alkyl group, an aryl group, a haloalkyl group, or a haloaryl group.

The compound represented by the formula (7-1) is preferably at least one compound selected from the group consisting of triphenylsulfonium trifluoromethanesulfonate, triphenylsulfonium nonafluoro-n-butanesulfonate, diphenyltolylsulfonium nonafluoro-n-butanesulfonate, triphenylsulfonium perfluoro-n-octanesulfonate, diphenyl-4-methylphenylsulfonium trifluoromethanesulfonate, di-2,4,6-trimethylphenylsulfonium trifluoromethanesulfonate, diphenyl-4-t-butoxyphenylsulfonium trifluoromethanesulfonate, diphenyl-4-t-butoxyphenylsulfonium nonafluoro-n-butanesulfonate, diphenyl-4-hydroxyphenylsulfonium trifluoromethanesulfonate, bis(4-fluorophenyl)-4-hydroxyphenylsulfonium trifluoromethanesulfonate, diphenyl-4-hydroxyphenylsulfonium nonafluoro-n-butanesulfonate, bis(4-hydroxyphenyl)-phenylsulfonium trifluoromethanesulfonate, tri(4-methoxyphenyl)sulfonium trifluoromethanesulfonate, tri(4-fluorophenyl)sulfonium trifluoromethanesulfonate, triphenylsulfonium p-toluenesulfonate, triphenylsulfonium benzenesulfonate, diphenyl-2,4,6-trimethylphenyl-p-toluenesulfonate, diphenyl-2,4,6-trimethylphenylsulfonium 2-trifluoromethylbenzenesulfonate, diphenyl-2,4,6-trimethylphenylsulfonium 4-trifluoromethylbenzenesulfonate, diphenyl-2,4,6-trimethylphenylsulfonium-2,4-difluorobenzenesulfonate, diphenyl-2,4,6-trimethylphenylsulfonium hexafluorobenzenesulfonate, diphenylnaphthylsulfonium trifluoromethanesulfonate, diphenyl-4-hydroxyphenylsulfonium p-toluenesulfonate, triphenylsulfonium 10-camphorsulfonate, diphenyl-4-hydroxyphenylsulfonium 10-camphorsulfonate, and cyclo(1,3-perfluoropropanedisulfon)imidate.

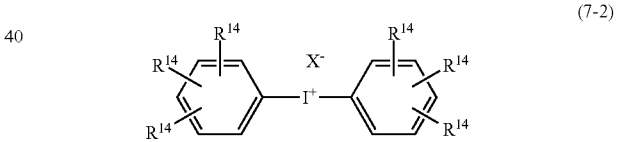

(7-2)

wherein $R^{14}$ groups may be the same or different, and each independently a hydrogen atom, a linear, branched or cyclic alkyl group, a linear, branched or cyclic alkoxy group, hydroxyl group or halogen atom, and $X^-$ is the same as defined above.

The compound represented by formula (7-2) is preferably at least one compound selected from the group consisting of bis(4-t-butylphenyl)iodonium trifluoromethanesulfonate, bis(4-t-butylphenyl)iodonium nonafluoro-n-butanesulfonate, bis(4-t-butylphenyl)iodonium perfluoro-n-octanesulfonate, bis(4-t-butylphenyl)iodonium p-toluenesulfonate, bis(4-t-butylphenyl)iodonium benzenesulfonate, bis(4-t-butylphenyl)iodonium-2-trifluoromethylbenzenesulfonate, bis(4-t-butylphenyl)iodonium 4-trifluoromethylbenzenesulfonate, bis(4-t-butylphenyl)iodonium 2,4-difluorobenzenesulfonate, bis(4-t-butylphenyl)iodonium hexafluorobenzenesulfonate, bis(4-t-butylphenyl)iodonium 10-camphorsulfonate, diphenyliodonium trifluoromethanesulfonate, diphenyliodonium nonafluoro-n-butanesulfonate, diphenyliodonium perfluoro-n-octanesulfonate, diphenyliodonium p-toluenesulfonate, diphenyliodonium benzenesulfonate, diphenyliodonium 10-camphorsulfonate, diphenyliodonium 2-trifluoromethylbenzenesulfonate, diphenyliodonium 4-trifluoromethylbenzenesulfonate, diphenyliodonium 2,4-difluorobenzenesulfonate, diphenyliodonium hexafluorobenzenesulfonate, di(4-trifluoromethylphenyl)iodonium trifluoromethanesulfonate, di(4-trifluoromethylphenyl)iodonium nonafluoro-n-butanesulfonate, di(4-trifluoromethylphenyl)iodonium perfluoro-n-octanesulfonate, di(4-trifluoromethylphenyl)iodonium p-toluenesulfonate, di(4-trifluoromethylphenyl)iodonium benzenesulfonate, and di(4-trifluoromethylphenyl)iodonium 10-camphorsulfonate.

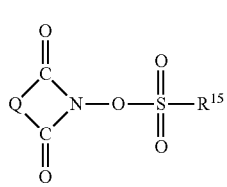

(7-3)

wherein Q is an alkylene group, an arylene group or an alkoxylene group, and $R^{15}$ is an alkyl group, an aryl group, a halogen-substituted alkyl group or a halogen-substituted aryl group.

The compound represented by formula (7-3) is preferably at least one compound selected from the group consisting of N-(trifluoromethylsulfonyloxy)succinimide, N-(trifluoromethylsulfonyloxy)phthalimide, N-(trifluoromethylsulfonyloxy)diphenylmaleimide, N-(trifluoromethylsulfonyloxy)bicyclo[2.2.1]hept-5-ene-2,3-dicarboxyimide, N-(trifluoromethylsulfonyloxy)naphthylimide, N-(10-camphorsulfonyloxy)succinimide, N-(10-camphorsulfonyloxy)phthalimide, N-(10-camphorsulfonyloxy)diphenylmaleimide, N-(10-camphorsulfonyloxy)bicyclo[2.2.1]hept-5-ene-2,3-dicarboxyimide, N-(10-camphorsulfonyloxy)naphthylimide, N-(n-octanesulfonyloxy)bicyclo[2.2.1]hept-5-ene-2,3-dicarboxyimide, N-(n-octanesulfonyloxy)naphthylimide, N-(p-toluenesulfonyloxy)bicyclo[2.2.1]hept-5-ene-2,3-dicarboxyimide, N-(p-toluenesulfonyloxy)naphthylimide, N-(2-trifluoromethylbenzenesulfonyloxy)bicyclo[2.2.1]hept-5-ene-2,3-dicarboxyimide, N-(2-trifluoromethylbenzenesulfonyloxy)naphthylimide, N-(4-trifluoromethylbenzenesulfonyloxy)bicyclo[2.2.1]hept-5-ene-2,3-dicarboxyimide, N-(4-trifluoromethylbenzenesulfonyloxy)naphthylimide, N-(perfluorobenzenesulfonyloxy)bicyclo[2.2.1]hept-5-ene-2,3-dicarboxyimide, N-(perfluorobenzenesulfonyloxy)naphthylimide, N-(1-naphthalenesulfonyloxy)bicyclo[2.2.1]hept-5-ene-2,3-dicarboxyimide, N-(1-naphthalenesulfonyloxy)naphthylimide, N-(nonafluoro-n-butanesulfonyloxy)bicyclo[2.2.1]hept-5-ene-2,3-dicarboxyimide, N-(nonafluoro-n-butanesulfonyloxy)naphthylimide, N-(perfluoro-n-octanesulfonyloxy)bicyclo[2.2.1]hept-5-ene-2,3-dicarboxyimide, and N-(perfluoro-n-octanesulfonyloxy)naphthylimide.

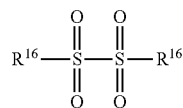

(7-4)

wherein $R^{16}$ groups may be the same or different, and each independently an optionally substituted linear, branched or cyclic alkyl group, an optionally substituted aryl group, an optionally substituted heteroaryl group or an optionally substituted aralkyl group.

The compound represented by formula (7-4) is preferably at least one compound selected from the group consisting of diphenyl disulfone, di(4-methylphenyl) disulfone, dinaphthyl disulfone, di(4-tert-butylphenyl) disulfone, di(4-hydroxyphenyl) disulfone, di(3-hydroxynaphthyl) disulfone, di(4-fluorophenyl) disulfone, di(2-fluorophenyl)disulfone, and di(4-trifluoromethylphenyl) disulfone.

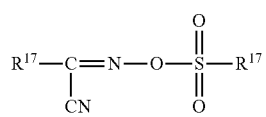

(7-5)

wherein $R^{17}$ groups may be the same or different, and each independently an optionally substituted linear, branched or cyclic alkyl group, an optionally substituted aryl group, an optionally substituted heteroaryl group or an optionally substituted aralkyl group.

The compound represented by formula (7-5) is at least one compound selected from the group consisting of α-(methylsulfonyloxyimino)phenylacetonitrile, α-(methylsulfonyloxyimino)-4-methoxyphenylacetonitrile, α-(trifluoromethylsulfonyloxyimino)phenylacetonitrile, α-(trifluoromethylsulfonyloxyimino)-4-methoxyphenylacetonitrile, α-(ethylsulfonyloxyimino)-4-methoxyphenylacetonitrile, α-(propylsulfonyloxyimino)-4-methylphenylacetonitrile, and α-(methylsulfonyloxyimino)-4-bromophenylacetonitrile.

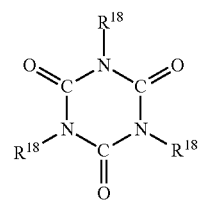

(7-6)

wherein $R^{18}$ groups may be the same or different, and each independently a haloalkyl group having one or more chlorine atoms and one or more bromine atoms. The haloalkyl group preferably has 1 to 5 carbon atoms.

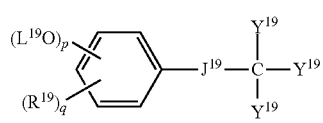

(7-7)

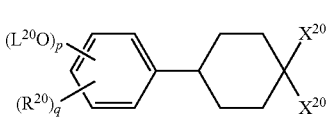

(7-8)

wherein $R^{19}$ groups and $R^{20}$ groups are each independently an alkyl group having 1 to 3 carbon atoms, such as methyl group, ethyl group, n-propyl group, and isopropyl group; a cycloalkyl group, such as cyclopentyl group and cyclohexyl group; an alkoxy group having 1 to 3 carbon atoms, such as methoxy group, ethoxy group, and propoxy group; or an aryl group, such as phenyl group, tolyl group, and naphthyl group, preferably an aryl group having 6 to 10 carbon atoms. $L^{19}$ groups and $L^{20}$ groups are each independently an organic group having a 1,2-naphthoquinonediazido group. Preferred examples thereof include 1,2-quinonediazidosulfonyl groups, such as 1,2-naphthoquinonediazido-4-sulfonyl group, 1,2-naphthoquinonediazido-5-sulfonyl group, and 1,2-naphthoquinonediazido-6-sulfonyl group, with 1,2-naphthoquinonediazido-4-sulfonyl group and 1,2-naphthoquinonediazido-5-sulfonyl group being particularly preferred. Subscript p is an integer of 1 to 3, and q is an integer of 0 to 4, satisfying 1≤p+q≤5. $J^{19}$ is a single bond, a polymethylene group having 1 to 4 carbon atoms, a cycloalkylene group, phenylene group, a group represented by formula (7-7-1), carbonyl group, an ester group, an amide group, or an ether group. $Y^{19}$ is a hydrogen atom, an alkyl group or an aryl group and each $X^{20}$ is independently a group represented by formula (7-8-1).

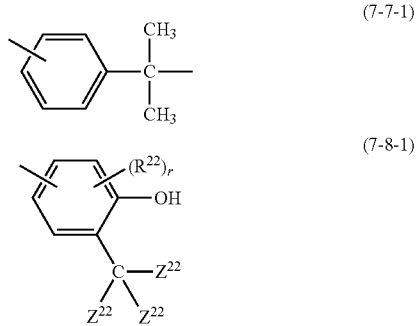

wherein each $Z^{22}$ is independently an alkyl group, a cycloalkyl group or an aryl group, $R^{22}$ is an alkyl group, a cycloalkyl group or an alkoxy group, and r is an integer of 0 to 3.

Examples of other acid generators include bissulfonyldiazomethanes, such as bis(p-toluenesulfonyl)diazomethane, bis(2,4-dimethylphenylsulfonyl)diazomethane, bis(tert-butylsulfonyl)diazomethane, bis(n-butylsulfonyl)diazomethane, bis(isobutylsulfonyl)diazomethane, bis(isopropylsulfonyl)diazomethane, bis(n-propylsulfonyl)diazomethane, bis(cyclohexylsulfonyl)diazomethane, bis(isopropylsulfonyl)diazomethane, 1,3-bis(cyclohexylsulfonylazomethylsulfonyl)propane, 1,4-bis(phenylsulfonylazomethylsulfonyl)butane, 1,6-bis(phenylsulfonylazomethylsulfonyphexane, and 1,10-bis(cyclohexylsulfonylazomethylsulfonyl)decane; and halotriazine derivatives, such as 2-(4-methoxyphenyl)-4,6-(bistrichloromethyl)-1,3,5-triazine, 2-(4-methoxynaphthyl)-4,6-(bistrichloromethyl)-1,3,5-triazine, tris(2,3-dibromopropyl)-1,3,5-triazine, and tris(2,3-dibromopropyl) isocyanurate.

Preferred acid generators are those having an aromatic ring and the acid generator represented by formula (7-1) or (7-2) is more preferred. The acid generator represented by formula (7-1) or (7-2) wherein $X^-$ is an sulfonic acid ion having an aryl group or a halogen-substituted aryl group is still more preferred, and the acid generator having a sulfonic acid ion which has an aryl group is particularly preferred. Specifically, particularly preferred are diphenyltrimethylphenylsulfonium p-toluenesulfonate, triphenylsulfonium p-toluenesulfonate, triphenylsulfonium trifluoromethanesulfonate, and triphenylsulfonium nonafluoromethanesulfonate. Using the acid generator, LER can be reduced. The acid generator (C) may be used alone or in combination of two or more.

The radiation-sensitive composition of the invention preferably contains at least one acid crosslinking agent (G). The acid crosslinking agent (G) is a compound capable of intramolecularly or intermolecularly crosslinking the cyclic compound of formula (1) in the presence of the acid generated from the acid generator (C). Examples of such crosslinking agent (G) include compounds having at least one group (crosslinkable group) which crosslinks the cyclic compound of formula (1).

Examples of the crosslinkable group include (i) hydroxyalkyl groups or groups derived therefrom, such as a hydroxy (C1-C6 alkyl) group, a C1-C6 alkoxy(C1-C6 alkyl) group, and an acetoxy(C1-C6 alkyl) group; (ii) carbonyl groups or groups derived therefrom, such as formyl group and a carboxy(C1-C6 alkyl) group; (iii) groups having a nitrogen-containing group, such as dimethylaminomethyl group, diethylaminomethyl group, dimethylolaminomethyl group, diethylolaminomethyl group, and morpholinomethyl group; (iv) glycidyl group-containing groups, such as glycidyl ether group, glycidyl ester group, and glycidylamino group; (v) groups, such as benzyloxymethyl group and benzoyloxymethyl group, which are derived from aromatic groups, such as C1-C6 aryloxy(C1-C6 alkyl) group and C1-C6 aralkyloxy (C1-C6 alkyl) group; and (vi) groups having a polymerizable multiple bond, such as vinyl group and isopropenyl group, with a hydroxyalkyl group and an alkoxyalkyl group being preferred, and an alkoxymethyl group being particularly preferred.

Examples of the acid crosslinking agent (G) having the crosslinkable group include (i) methylol group-containing compounds, such as methylol group-containing melamine compounds, methylol group-containing benzoguanamine compounds, methylol group-containing urea compounds, methylol group-containing glycoluril compounds, and methylol group-containing phenol compounds; (ii) alkoxyalkyl group-containing compounds, such as alkoxyalkyl group-containing melamine compounds, alkoxyalkyl group-containing benzoguanamine compounds, alkoxyalkyl group-containing urea compounds, alkoxyalkyl group-containing glycoluril compounds, and alkoxyalkyl group-containing phenol compounds; (iii) carboxymethyl group-containing compounds, such as carboxymethyl group-containing melamine compounds, carboxymethyl group-containing benzoguanamine compounds, carboxymethyl group-containing urea compounds, carboxymethyl group-containing glycoluril compounds, and carboxymethyl group-containing phenol compounds; and (iv) epoxy compounds, such as bisphenol A-type epoxy compounds, bisphenol F-type epoxy compounds, bisphenol S-type epoxy compounds, novolak resin-type epoxy compounds, resol resin-type epoxy compounds, and poly(hydroxystyrene)-type epoxy compounds.

Other examples of the acid crosslinking agent (G) include compounds having a phenolic hydroxyl group and alkali-soluble resins which are provided with the crosslinking ability by the introduction of the crosslinkable group described above into their acid functional groups. The degree of introduction of the crosslinkable group is generally 5 to 100 mol %, preferably 10 to 60 mol %, and still more preferably 15 to 40 mol %, each based on the total of the acid functional groups in the compounds having a phenolic hydroxyl group and the alkali-soluble resins. Within the above range, the crosslinking reaction proceeds sufficiently to preferably reduce the film residue and prevent the patters from being swelled and made serpentine.

In the radiation-sensitive composition of the invention, the acid crosslinking agent (G) is preferably an alkoxyalkylated urea compound or its resin, or an alkoxyalkylated glycoluril compound or its resin. Particularly preferred acid crosslinking agent (G) (acid crosslinking agent (G1)) is the compounds represented by formulae (8-1) to (8-3) and the alkoxymethylated melamine compounds.

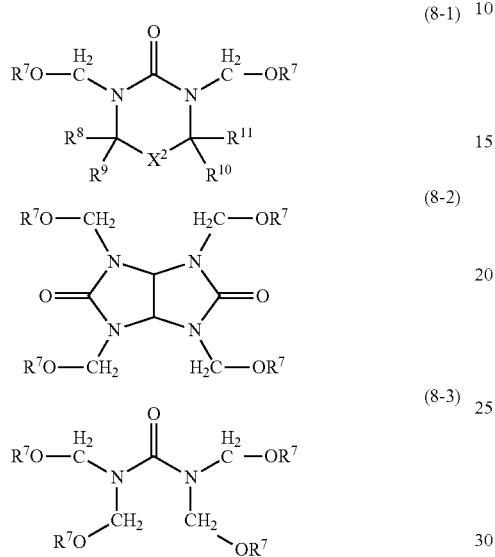

(8-1)

(8-2)

(8-3)

wherein each $R^7$ is independently a hydrogen atom, an alkyl group, or an acyl group; $R^8$ to $R^{11}$ are each independently a hydrogen atom, hydroxyl group, an alkyl group, or an alkoxyl group; and $X^2$ is a single bond, methylene group, or oxygen atom.

The alkyl group for $R^7$ has preferably 1 to 6 carbon atoms and more preferably 1 to 3 carbon atoms, and examples thereof include methyl group, ethyl group, and propyl group. The acyl group for $R^7$ has preferably 2 to 6 carbon atoms and more preferably 2 to 4 carbon atoms, and examples thereof include acetyl group and propionyl group. The alkyl group for each of $R^8$ to $R^{11}$ has preferably 1 to 6 carbon atoms and more preferably 1 to 3 carbon atoms, and examples thereof include methyl group, ethyl group, and propyl group. The alkoxyl group for each of $R^8$ to $R^{11}$ has preferably 1 to 6 carbon atoms and more preferably 1 to 3 carbon atoms, and examples thereof include methoxy group, ethoxy group, and propoxy group. $X^2$ is preferably a single bond or methylene group. $R^7$ to $R^{11}$ and $X^2$ may be substituted, for example, by an alkyl group, such as methyl group and ethyl group, an alkoxy group, such as methoxy group and ethoxy group, hydroxyl group, halogen atom, etc. Two or more $R^7$ and $R^8$ to $R^{11}$ are respectively the same or different.

Specific examples of the compounds of formula (8-1) include the following compounds:

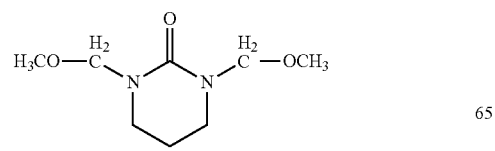

-continued

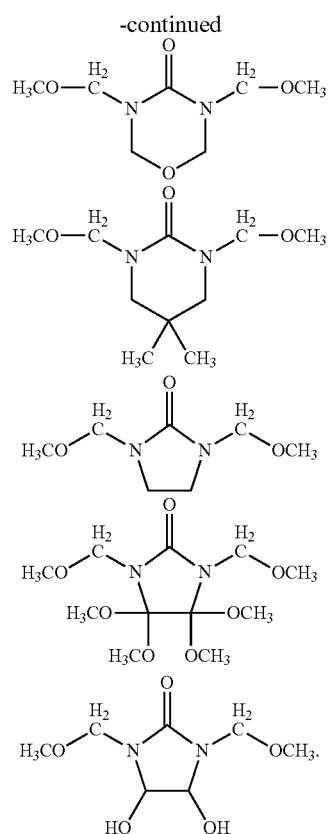

Specific examples of the compounds of formula (8-2) include N,N,N,N-tetra(methoxymethyl)glycoluril, N,N,N, N-tetra(ethoxymethyl)glycoluril, N,N,N,N-tetra(n-propoxymethyl)glycoluril, N,N,N,N-tetra(isopropoxymethyl) glycoluril, N,N,N,N-tetra(n-butoxymethyl)glycoluril, and N,N,N,N-tetra(t-butoxymethyl)glycoluril, with N,N,N,N-tetra(methoxymethyl)glycoluril being preferred.

Specific examples of the compounds of formula (8-3) include the following compounds:

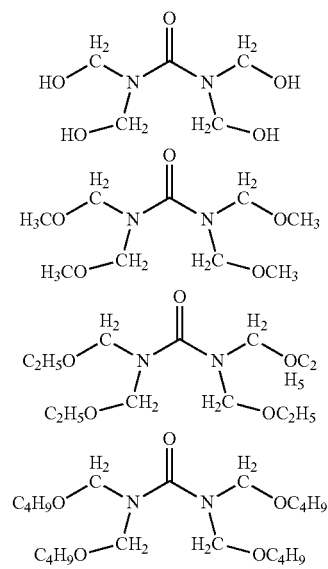

-continued

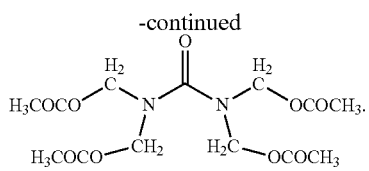

Examples of the alkoxymethylated melamine compound include N,N,N,N,N,N-hexa(methoxymethyl)melamine, N,N,N,N,N,N-hexa(ethoxymethyl)melamine, N,N,N,N,N,N-hexa(n-propoxymethyl)melamine, N,N,N,N,N,N-hexa(isopropoxymethyl)melamine, N,N,N,N,N,N-hexa(n-butoxymethyl)melamine, and N,N,N,N,N,N-hexa(t-butoxymethyl)melamine, with N,N,N,N,N,N-hexa(methoxymethyl)melamine being particularly preferred.

The acid crosslinking agent (G1) is produced, for example, by introducing methylol group into a urea compound or glycoluril compound by a condensation reaction with formalin, etherifying the resultant compound with an lower alcohol, such as methyl alcohol, ethyl alcohol, propyl alcohol, and butyl alcohol, and then recovering the compound or its resin precipitated by cooling the reaction product solution. The acid crosslinking agent (G1) is also commercially available under tradenames, such as "Cymel" (manufactured by Mitsui Cyanamid Co., Ltd.) and "Nikalac" (manufactured by Sanwa Chemical Co., Ltd.).

Other preferred acid crosslinking agent (G) (acid crosslinking agent (G2)) are phenol derivatives having in the molecule from 1 to 6 benzene rings and two or more hydroxyalkyl groups and/or alkoxyalkyl groups, wherein the hydroxyalkyl groups and/or alkoxyalkyl groups are bonded to one or more of the benzene rings. More preferred are phenol derivatives with a molecular weight of 1500 or less having in the molecule from 1 to 6 benzene rings and two or more hydroxyalkyl groups and/or alkoxyalkyl groups, wherein the hydroxyalkyl groups and/or alkoxyalkyl groups are bonded to one or more of the benzene rings.

The hydroxyalkyl group to be bonded to the benzene ring is preferably a $C_{1-6}$ group, such as hydroxymethyl group, 2-hydroxyethyl group, and 2-hydroxy-1-propyl group. The alkoxyalkyl group to be bonded to the benzene ring is preferably a $C_{2-6}$ group, such as methoxymethyl group, ethoxymethyl group, n-propoxymethyl group, isopropoxymethyl group, n-butoxymethyl group, isobutoxymethyl group, sec-butoxymethyl group, t-butoxymethyl group, 2-methoxyethyl group, and 2-methoxy-1-propyl group.

Particularly referred phenol derivatives are following compounds.

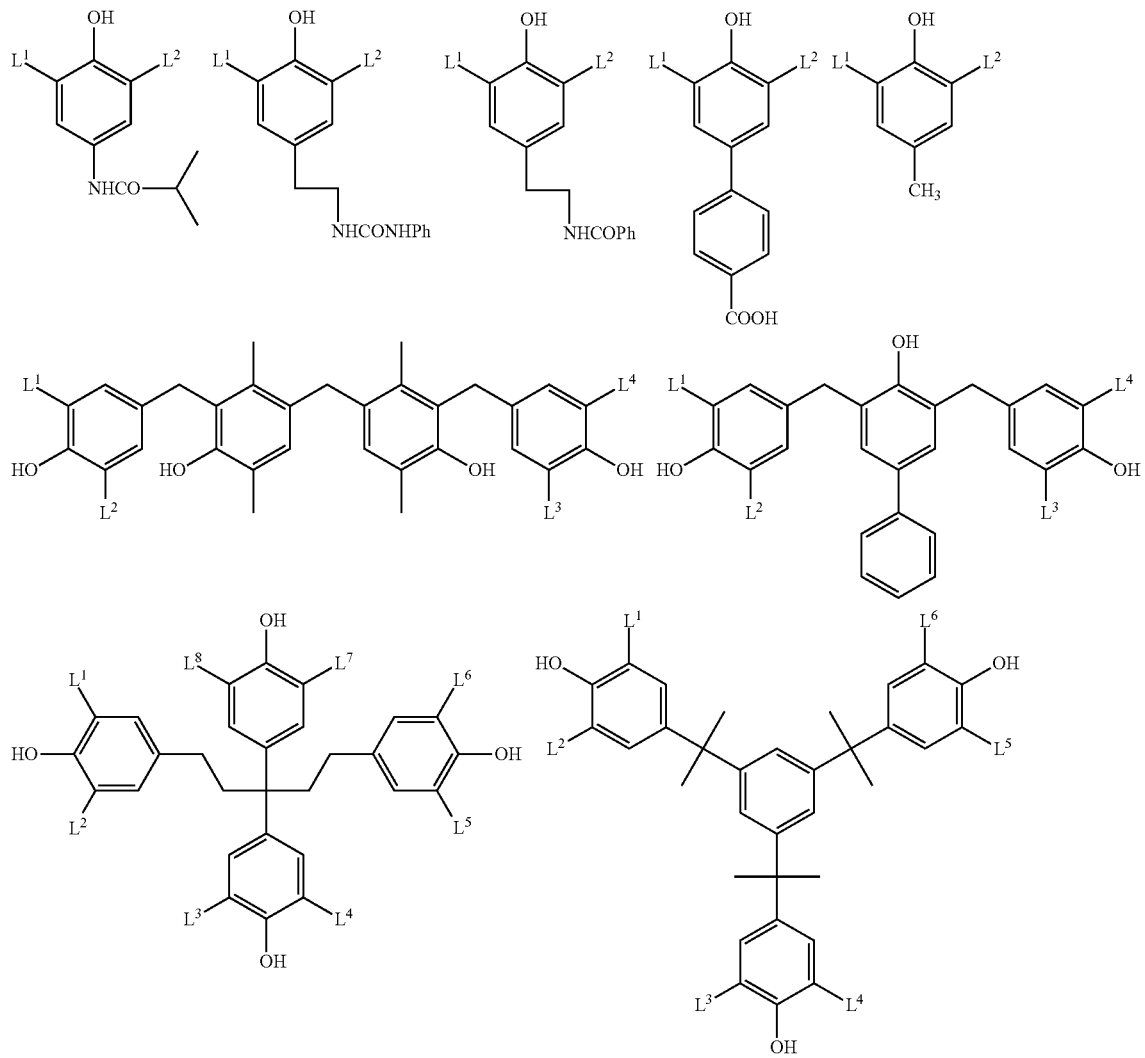

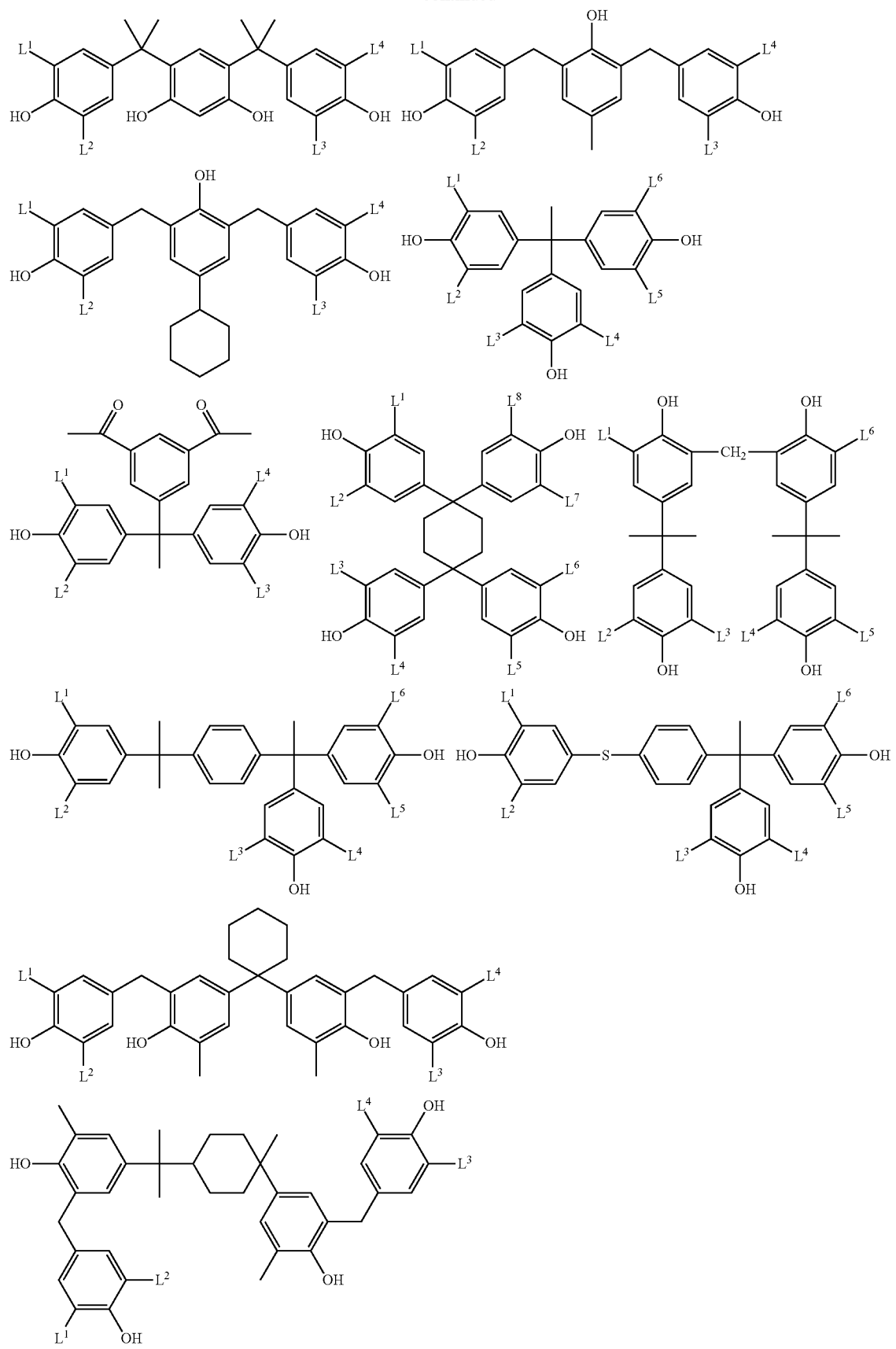

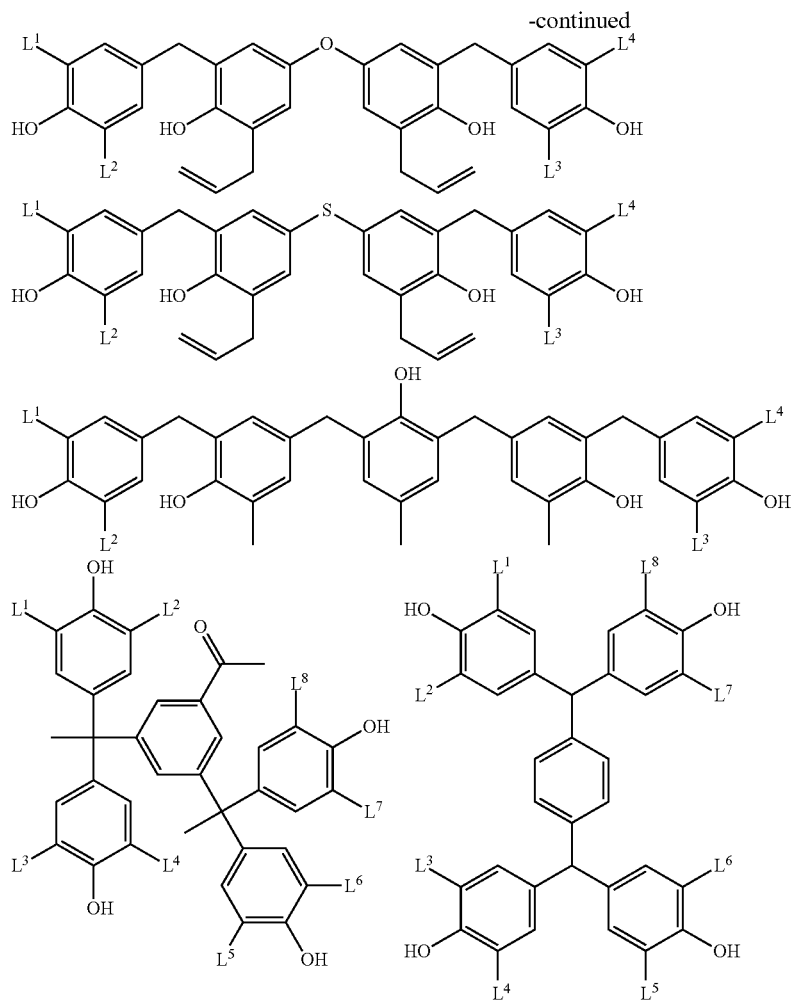

In the above formulas, $L^1$ to $L^8$ are the same or different and each independently a hydroxymethyl group, methoxymethyl group or ethoxymethyl group. The phenol derivative having a hydroxymethyl group is produced by the reaction of a corresponding phenol compound having no hydroxymethyl group (compound of the above formula in which $L^1$ to $L^8$ are each a hydrogen atom) with formaldehyde in the presence of a basic catalyst. The reaction is preferably performed at 60° C. or lower to prevent the product from being made resinous or gelated. For example, the reaction is produced by a method described in JP 6-282067A or JP 7-64285A.

The phenol derivative having an alkoxymethyl group is produced by the reaction of a corresponding phenol derivative having a hydroxymethyl group and an alcohol in the presence of an acid catalyst. The reaction is preferably performed at 100° C. or lower to prevent the product from being made resinous or gelated. For example, the reaction is produced by a method described in EP 632003A1.

The phenol derivative having the hydroxymethyl groups and/or alkoxymethyl groups produced in the above manner is excellent in the storage stability, and the phenol derivative having the alkoxymethyl groups is particularly preferred in view of the storage stability. The acid crosslinking agent (G2) may be used alone or in combination of two or more.

Still other preferred acid crosslinking agent (G) (acid crosslinking agent (G3)) are compounds having at least one α-hydroxyisopropyl group. The structure of such compounds is not specifically limited as far as the compounds have the a-hydroxyisopropyl group. The hydrogen atoms in the hydroxyl groups of the a-hydroxyisopropyl groups may be replaced by at least one acid-dissociating group, such as R—COO— and R—SO$_2$—, wherein R is a group selected from the group consisting of $C_{1-12}$ linear hydrocarbon group, $C_{3-12}$ cyclic hydrocarbon group, $C_{1-12}$ alkoxy group, $C_{3-12}$ 1-branched alkyl group, and $C_{6-12}$ aromatic hydrocarbon group. Examples of the compound having the a-hydroxyisopropyl group may be at least one compound selected from substituted or non-substituted aromatic compounds, diphenyl compounds, naphthalene compounds, and furan compounds, each having at least one α-hydroxyisopropyl group. Specific examples thereof are the compound of formula (9-1) (benzene compound (1)), the compound of formula (9-2) (diphenyl compound (2)), the compound of formula (9-3) (naphthalene compound (3)), and the compound of formula (9-4) (furan compound (4)).

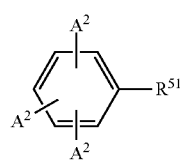

(9-1)

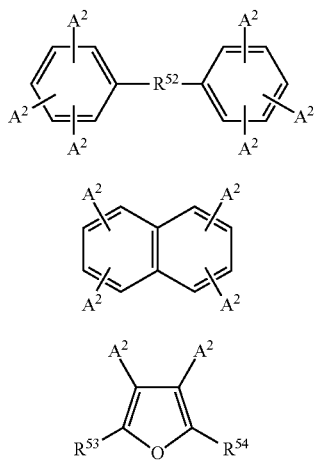

Each $A^2$ in formulae (9-1) to (9-4) is independently an α-hydroxyisopropyl group or hydrogen atom, and at least one $A^2$ is the α-hydroxyisopropyl group. In formula (9-1), $R^{51}$ is a hydrogen atom, hydroxyl group, $C_{2-6}$ linear or branched alkylcarbonyl group, or $C_{2-6}$ linear or branched alkoxycarbonyl group. In formula (9-2), $R^{52}$ is a single bond, $C_{1-5}$ linear or branched alkylene group, —O—, —CO—, or —COO—. In formula (9-4), $R^{53}$ and $R^{54}$ are each independently a hydrogen atom or $C_{1-6}$ linear or branched alkyl group.

Examples of the benzene compound (1) include α-hydroxyisopropylbenzenes, such as α-hydroxyisopropylbenzene, 1,3-bis(α-hydroxyisopropyl)benzene, 1,4-bis(α-hydroxyisopropyl)benzene, 1,2,4-tris(α-hydroxyisopropyl)benzene, and 1,3,5-tris(α-hydroxyisopropyl)benzene; α-hydroxyisopropylphenols, such as 3-α-hydroxyisopropylphenol, 4-α-hydroxyisopropylphenol, 3,5-bis(α-hydroxyisopropyl)phenol, and 2,4,6-tris(α-hydroxyisopropyl)phenol; α-hydroxyisopropylphenyl alkyl ketones, such as 3-α-hydroxyisopropylphenyl methyl ketone, 4-α-hydroxyisopropylphenyl methyl ketone, 4-α-hydroxyisopropylphenyl ethyl ketone, 4-α-hydroxyisopropylphenyl n-propyl ketone, 4-α-hydroxyisopropylphenyl isopropyl ketone, 4-α-hydroxyisopropylphenyl n-butyl ketone, 4-α-hydroxyisopropylphenyl t-butyl ketone, 4-α-hydroxyisopropylphenyl n-pentyl ketone, 3,5-bis(α-hydroxyisopropyl)phenyl methyl ketone, 3,5-bis(α-hydroxyisopropyl)phenyl ethyl ketone, and 2,4,6-tris(α-hydroxyisopropyl)phenyl methyl ketone; and alkyl 4-α-hydroxyisopropylbenzoates, such as methyl 3-α-hydroxyisopropylbenzoate, methyl 4-α-hydroxyisopropylbenzoate, ethyl 4-α-hydroxyisopropylbenzoate, n-propyl 4-α-hydroxyisopropylbenzoate, isopropyl 4-α-hydroxyisopropylbenzoate, n-butyl 4-α-hydroxyisopropylbenzoate, t-butyl 4-α-hydroxyisopropylbenzoate, n-pentyl 4-α-hydroxyisopropylbenzoate, methyl 3,5-bis(α-hydroxyisopropyl)benzoate, ethyl 3,5-bis(α-hydroxyisopropyl)benzoate, and methyl 2,4,6-tris(α-hydroxyisopropyl)benzoate.

Examples of the diphenyl compound (2) include α-hydroxyisopropylbiphenyls, such as 3-α-hydroxyisopropylbiphenyl, 4-α-hydroxyisopropylbiphenyl, 3,5-bis(α-hydroxyisopropyl)biphenyl, 3,3'-bis(α-hydroxyisopropyl)biphenyl, 3,4'-bis(α-hydroxyisopropyl)biphenyl, 4,4'-bis(α-hydroxyisopropyl)biphenyl, 2,4,6-tris(α-hydroxyisopropyl)biphenyl, 3,3',5-tris(α-hydroxyisopropyl)biphenyl, 3,4',5-tris(α-hydroxyisopropyl)biphenyl, 2,3'4,6-tetrakis(α-hydroxyisopropyl)biphenyl, 2,4,4',6-tetrakis(α-hydroxyisopropyl)biphenyl, 3,3'5,5'-tetrakis(α-hydroxyisopropyl)biphenyl, 2,3',4,5',6-pentakis(α-hydroxyisopropyl)biphenyl, and 2,2',4,4',6,6'-hexakis(α-hydroxyisopropyl)biphenyl;

α-hydroxyisopropyldiphenylalkanes, such as 3-α-hydroxyisopropyldiphenylmethane, 4-α-hydroxyisopropyldipehnylmethane, 1-(4-α-hydroxyisopropylphenyl)-2-phenylethane, 1-(4-α-hydroxyisopropylphenyl)-2-phenylpropane, 2-(4-α-hydroxyisopropylphenyl)-2-phenylpropane, 1-(4-α-hydroxyisopropylphenyl)-3-phenylpropane, 1-(4-α-hydroxyisopropylphenyl)-4-phenylbutane, 1-(4-α-hydroxyisopropylphenyl)-5-phenylpentane, 3,5-bis(α-hydroxyisopropyldiphenylmethane, 3,3'-bis(α-hydroxyisopropyl)diphenylmethane, 3,4'-bis(α-hydroxyisopropyl)diphenylmethane, 4,4'-bis(α-hydroxyisopropyl)diphenylmethane, 1,2-bis(4-α-hydroxyisopropylphenyl)ethane, 1,2-bis(4-α-hydroxypropylphenyl)propane, 2,2-bis(4-α-hydroxypropylphenyl)propane, 1,3-bis(4-α-hydroxypropylphenyl)propane, 2,4,6-tris(α-hydroxyisopropyl)diphenylmethane, 3,3',5-tris(α-hydroxyisopropyl)diphenylmethane, 3,4',5-tris(α-hydroxyisopropyl)diphenylmethane, 2,3',4,6-tetrakis(α-hydroxyisopropyl)diphenylmethane, 2,4,4',6-tetrakis(α-hydroxyisopropyl)diphenylmethane, 3,3',5,5'-tetrakis(α-hydroxyisopropyl)diphenylmethane, 2,3',4,5',6-pentakis(α-hydroxyisopropyl)diphenylmethane, and 2,2',4,4',6,6'-hexakis(α-hydroxyisopropyl)diphenylmethane;

α-hydroxyisopropyldiphenyl ethers, such as 3-α-hydroxyisopropyldipehnyl ether, 4-α-hydroxyisopropyldiphenyl ether, 3,5-bis(α-hydroxyisopropyl)diphenyl ether, 3,3'-bis(α-hydroxyisopropyl)diphenyl ether, 3,4'-bis(α-hydroxyisopropyl)diphenyl ether, 4,4'-bis(α-hydroxyisopropyl)diphenyl ether, 2,4,6-tris(α-hydroxyisopropyl)diphenyl ether, 3,3',5-tris(α-hydroxyisopropyl)diphenyl ether, 3,4',5-tris(α-hydroxyisopropyl)diphenyl ether, 2,3',4,6-tetrakis(α-hydroxyisopropyl)diphenyl ether, 2,4,4'6-tetrakis(α-hydroxyisopropyl)diphenyl ether, 3,3',5,5'-tetrakis(α-hydroxyisopropyl)diphenyl ether, 2,3',4,5',6-pentakis(α-hydroxyisopropyl)diphenyl ether, and 2,2',4,4',6,6'-hexakis(α-hydroxyisopropyl)diphenyl ether;

α-hydroxyisopropyldiphenyl ketones, such as 3-α-hydroxyisopropyldiphenyl ketone, 4-α-hydroxyisopropyldiphenyl ketone, 3,5-bis(α-hydroxyisopropyl)diphenyl ketone, 3,3'-bis(α-hydroxyisopropyl)diphenyl ketone, 3,4'-bis(α-hydroxyisopropyl)diphenyl ketone, 4,4'-bis(α-hydroxyisopropyl)diphenyl ketone, 2,4,6-tris(α-hydroxyisopropyl)diphenyl ketone, 3,3',5-tris(α-hydroxyisopropyl)diphenyl ketone, 3,4',5-tris(α-hydroxyisopropyl)diphenyl ketone, 2,3',4,6-tetrakis(α-hydroxyisopropyl)diphenyl ketone, 2,4,4',6-tetrakis(α-hydroxyisopropyl)diphenyl ketone, 3,3',5,5'-tetrakis(α-hydroxyisopropyl)diphenyl ketone, 2,3',4,5',6-pentakis(α-hydroxyisopropyl)diphenyl ketone, and 2,2',4,4',6,6'-hexakis(α-hydroxyisopropyl)diphenyl ketone; and phenyl α-hydroxyisopropylbenzoates, such as phenyl 3-α-hydroxyisopropylbenzoate, phenyl 4-α-hydroxyisopropylbenzoate, 3-α-hydroxyisopropylphenyl benzoate, 4-α-hydroxyisopropylphenyl benzoate, phenyl 3,5-bis(α-hydroxyisopropyl)benzoate, 3-α-hydroxyisopropylphenyl 3-α-hydroxyisopropylbenzoate, 4-α-hydroxyisopropylphenyl 3-α-hydroxyisopropylbenzoate, 3-α-hydroxyisopropylphenyl 4-α-hydroxyisopropylbenzoate, 4-α-hydroxyisopropylphenyl 4-α-hydroxyisopropylbenzoate, 3,5-bis(α- hydroxyisopropyl)phenyl benzoate, phenyl 2,4,6-tris(α-hydroxyisopropyl)benzoate, 3-α-hydroxyisopropylphenyl 3,5-bis(αhydroxyisopropyl)benzoate, 4-α-hydroxyisopropylphenyl 3,5-bis(α-hydroxyisopropyl)benzoate, 3,5-bis(α-hydroxyisopropyl)phenyl 3-α-hydroxyisopropylbenzoate, 3,5-bis(α-hydroxyisopropyl)phenyl 4-α-hydroxyisopropylbenzoate, 2,4,6-tris(α-hydroxyisopropyl)phenyl benzoate, 3-α-hydroxyisopropylphenyl 2,4,6-tris(α-hydroxyisopropyl)benzoate, 4-α-hydroxyisopropylphenyl 2,4,6-tris(α-hydroxyisopropyl)benzoate, 3,5-bis(α-hydroxyisopropyl)phenyl 3,5-bis-(α-hydroxyisopropyl)benzoate, 2,4,6-tris(α-hydroxyisopropyl)phenyl 3-α-hydroxyisopropylbenzoate, 2,4,6-tris(α-hydroxyisopropyl)phenyl 4-α-hydroxyisopropylbenzoate, 3,5-bis(α-hydroxyisopropyl)phenyl 2,4,6-tris (α-hydroxyisopropyl)benzoate, 2,4,6-tris(α-hydroxyisopropyl)phenyl 3,5-bis(α-hydroxyisopropyl)benzoate, and 2,4,6-tris(α-hydroxyisopropyl)phenyl 2,4,6-tris(α-hydroxyisopropyl)benzoate.

Examples of the naphthalene compound (3) include 1-(α-hydroxyisopropyl)naphthalene, 2-(α-hydroxyisopropyl) naphthalene, 1,3-bis(α-hydroxyisopropylnaphthalene, 1,4-bis(α-hydroxyisopropyl)naphthalene, 1,5-bis(α-hydroxyisopropylnaphthalene, 1,6-bis(α-hydroxyisopropyl) naphthalene, 1,7-bis(α-hydroxyisopropyl)naphthalene, 2,6-bis(α-hydroxyisopropyl)naphthalene, 2,7-bis(α-hydroxyisopropyl)naphthalene, 1,3,5-tris(α-hydroxyisopropyl)naphthalene, 1,3,6-tris(α-hydroxyisopropyl)naphthalene, 1,3,7-tris(α-hydroxyisopropyl)naphthalene, 1,4,6-tris(α-hydroxyisopropyl)naphthalene, 1,4,7-tris(α-hydroxyisopropyl)naphthalene, and 1,3,5,7-tetrakis(α-hydroxyisopropyl)naphthalene.

Examples of the furan compound (4) include 3-(α-hydroxyisopropyl)furan, 2-methyl-3-(α-hydroxyisopropyl)furan, 2-methyl-4-(α-hydroxyisopropyl)furan, 2-ethyl-4-(α-hydroxyisopropyl)furan, 2-n-propyl-4-(α-hydroxyisopropyl)furan, 2-isopropyl-4-(α-hydroxyisopropyl)furan, 2-n-butyl-4-(α-hydroxyisopropyl) furan, 2-t-butyl-4-(α-hydroxyisopropyl)furan, 2-n-pentyl-4-(α-hydroxyisopropyl)furan, 2,5-dimethyl-3-(α-hydroxyisopropyl)furan, 2,5-diethyl-3-(α-hydroxyisopropyl)furan, 3,4-bis(α-hydroxyisopropyl)furan, 2,5-dimethyl-3,4-bis(α-hydroxyisopropyl)furan, and 2,5-diethyl-3,4-bis(αhydroxyisopropyl)furan.

The acid crosslinking agent (G3) is preferably the compound having two or more free a-hydroxyisopropyl groups, more preferably the benzene compound (1) having two or more α-hydroxyisopropyl groups, the diphenyl compound (2) having two or more α-hydroxyisopropyl groups or the naphthalene compound (3) having two or more α-hydroxyisopropyl groups, and particularly preferably the α-hydroxyisopropylbiphenyl compound having two or more α-hydroxyisopropyl groups or the naphthalene compound (3) having two or more α-hydroxyisopropyl groups.

The acid crosslinking agent (G3) is generally produced by a method in which an acetyl group-containing compound, such as 1,3-diacetylbenzene, is methylated by a Grignard reagent, such as CH$_3$MgBr, and then hydrolyzed, or a method in which an isopropyl group-containing compound, such as 1,3-diisopropylbenzene, is converted into an peroxide by the oxidation by oxygen, etc. and then the peroxide is reduced.

The amount of the acid crosslinking agent (G) to be used is preferably 0.5 to 49% by weight, more preferably 0.5 to 40% by weight, still more preferably 1 to 30% by weight, and particularly preferably 2 to 20% by weight, each based on the total weight of the solid component. If being 0.5% by weight or more, the effect of controlling the solubility of the resist film in an alkali developer is enhanced, to prevent the reduction of film residue and prevent the patterns from being swelled and made serpentine. If being 50% by weight or less, the heat resistance of the resist is preferably prevented from being reduced.

The blending ratio of at least one component selected from the acid crosslinking agent (G1), acid crosslinking agent (G2), and acid crosslinking agent (G3) in the acid crosslinking agent (G) is not limited, and suitably determined according to the kind of substrate to be used in the formation of resist patterns.

The content of the alkoxymethylated melamine compound and/or the compounds of formulae (9-1) to (9-3) in the total acid crosslinking agent component is 50 to 99% by weight, preferably 60 to 99% by weight, more preferably 70 to 98% by weight, and still more preferably 80 to 97% by weight. If 50% by weight or more, the resolution is preferably improved. If 99% by weight or less, the cross section of the patterns is easily made into a rectangular shape.

The radiation-sensitive composition of the invention may include an acid-diffusion controller (E) which has an effect of inhibiting the undesirable chemical reactions in unexposed areas by preventing the acid generated from the acid generator upon the exposure to radiation from diffusing throughout the resist film. Using the acid-diffusion controller (E), the storage stability and resolution of the radiation-sensitive composition can be improved. In addition, the change of line width of resist patterns due to the variation of time delay before and after irradiation can be prevented, thereby to make the process stability extremely excellent. Examples of the acid-diffusion controller (E) include a radiation-decomposable basic compound, such as a nitrogen-containing basic compound, a basic sulfonium compound, and a basic iodonium compound. The acid-diffusion controller (E) may be used alone or in combination of two or more.

The acid-diffusion controller includes, for example, a nitrogen-containing organic compound and a basic compound which is decomposable upon the exposure to radiation. Examples of the nitrogen-containing organic compound include a compound of formula (10) (nitrogen-containing compound (I)):

(10)

a diamino compound having two nitrogen atoms in its molecule (nitrogen-containing compound (II)), a polyamino compound having three or more nitrogen atoms or its polymer (nitrogen-containing compound (III)), an amide group-containing compound, an urea compound, and a nitrogen-containing heterocyclic compound. The acid-diffusion controller (E) may be used alone or in combination of two or more.

In formula (10), $R^{61}$, $R^{62}$ and $R^{63}$ are each independently a hydrogen atom, linear, branched or cyclic alkyl group, aryl group, or aralkyl group. The alkyl group, aryl group, and aralkyl group may be non-substituted or substituted by another functional group, such as hydroxyl group. The linear, branched or cyclic alkyl group has 1 to 15 carbon atoms and preferably 1 to 10 carbon atoms. Examples thereof include methyl group, ethyl group, n-propyl group, isopropyl group, n-butyl group, isobutyl group, sec-butyl group, t-butyl group, n-pentyl group, neopentyl group, n-hexyl group, t-hexyl group, n-heptyl group, n-octyl group, n-ethylhexyl group, n-nonyl group, and n-decyl group. The aryl group may include a $C_{6-12}$ group such as phenyl group, tolyl group, xylyl group, cumenyl group, and 1-naphthyl group. The aralkyl group may include a $C_{7-19}$ group, preferably a $C_{7-13}$ group, such as benzyl group, α-methylbenzyl group, phenethyl group, and naphthylmethyl group.

Examples of the nitrogen-containing compound (I) include mono(cyclo)alkylamines, such as n-hexylamine, n-heptylamine, n-octylamine, n-nonylamine, n-decylamine, n-dodecylamine, and cyclohexylamine; di(cyclo)alkylamines, such as di-n-butylamine, di-n-pentylamine, di-n-hexylamine, di-n-heptylamine, di-n-octylamine, di-n-nonylamine, di-n-decylamine, methyl-n-dodecylamine, di-n-dodecylmethyl, cyclohexylmethylamine, and dicyclohexylamine; tri(cyclo)alkylamines, such as triethylamine, tri-n-propylamine, tri-n-butylamine, tri-n-pentylamine, tri-n-hexylamine, tri-n-heptylamine, tri-n-octylamine, tri-n-nonylamine, tri-n-decylamine, dimethyl-n-dodecylamine, di-n-dodecylmethylamine, dicyclohexylmethylamine, and tricyclohexylamine; alkanolamines, such as monoethanolamine, diethanolamine, and triethanolamine; and aromatic amines, such as aniline, N-methylaniline, N,N-dimethylaniline, 2-methylaniline, 3-methylaniline, 4-methylaniline, 4-nitroaniline, diphenylamine, triphenylamine, and 1-naphthylamine.

Examples of the nitrogen-containing compound (II) include ethylenediamine, N,N,N',N'-tetramethylethylenediamine, N,N,N',N'-tetrakis(2-hydroxypropypethylenediamine, tetramethylenediamine, hexamethylenediamine, 4,4'-diaminodiphenylmethane, 4,4'-diaminodiphenyl ether, 4,4'-diaminobenzophenone, 4,4'-diaminodiphenylamine, 2,2-bis(4-aminophenyl)propane, 2-(3-aminophenyl)-2-(4-aminophenyl)propane, 2-(4-aminophenyl)-2-(3-hydroxyphenyl)propane, 2-(4-aminophenyl)-2-(4-hydroxyphenyl)propane, 1,4-bis[1-(4-aminophenyl)-1-methylethyl]benzene, and 1,3-bis[1-(4-aminophenyl)-1-methylethyl]benzene.

Examples of the nitrogen-containing compound (III) include polyethyleneimine, polyarylamine, and polymer of N-(2-dimethylaminoethyl)acrylamide.

Examples of the amide group-containing compound include formamide, N-methylformamide, N,N-dimethylformamide, acetamide, N-methylacetamide, N,N-dimethylacetamide, propionamide, benzamide, pyrrolidone, and N-methylpyrrolidone.

Examples of the urea compound include urea, methylurea, 1,1-dimethylurea, 1,3-dimethylurea, 1,1,3,3-tetramethylurea, 1,3-diphenylurea, and tri-n-butylthiourea.

Examples of the nitrogen-containing heterocyclic compound include imidazoles, such as imidazole, benzimidazole, 4-methylimidazole, 4-methyl-2-phenylimidazole, and 2-phenylbenzimidazole; pyridines, such as pyridine, 2-methylpyridine, 4-methylpyridine, 2-ethylpyridine, 4-ethylpyridine, 2-phenylpyridine, 4-phenylpyridine, 2-methyl-4-phenylpyridine, nicotine, nicotinic acid, nicotinic amide, quinoline, 8-oxyquinoline, and acridine; and pyrazine, pyrazole, pyridazine, quinoxaline, purine, pyrrolidine, piperidine, morpholine, 4-methylmorpholine, piperazine, and 1,4-dimethylpiperazine, 1,4-diazabicyclo[2.2.2]octane.

Examples of the radiation-decomposable basic compound include a sulfonium compound represented by formula (11-1);

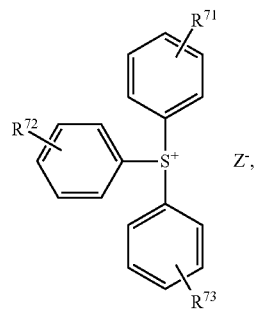

(11-1)

and an iodonium compound represented by formula (11-2);

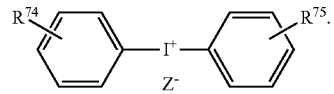

(11-2)

In the formulae (11-1) and (11-2), $R^{71}$, $R^{72}$, $R^{73}$, $R^{74}$, and $R^{75}$ are each independently a hydrogen atom, $C_{1-6}$ alkyl group, $C_{1-6}$ alkoxyl group, hydroxyl group or halogen atom. $Z^-$ is $HO^-$, R—$COO^-$ wherein R is a $C_{1-6}$ alkyl group, $C_{6-11}$ aryl group or $C_{7-12}$ alkaryl group, or anion represented by formula (11-3);

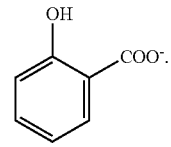

(11-3)

Specific examples of the radiation-decomposable basic compound include triphenylsulfonium hydroxide, triphenylsulfonium acetate, triphenylsulfonium salicylate, diphenyl-4-hydroxyphenylsulfonium hydroxide, diphenyl-4-hydroxyphenylsulfonium acetate, diphenyl-4-hydroxyphenylsulfonium salicylate, bis(4-t-butylphenyl)iodonium hydroxide, bis(4-t-butylphenyl)iodonium acetate, bis(4-t-butylphenyl)iodonium hydroxide, bis(4-t-butylphenyl)iodonium acetate, bis(4-t-butylphenyl)iodonium salicylate, 4-t-butylphenyl4-hydroxyphenyliodonium hydroxide, 4-t-butylphenyl4-hydroxyphenyliodonium acetate, and 4-t-butylphenyl4-hydroxyphenyliodonium salicylate.

The blending amount of the acid-diffusion controller (E) is preferably 0.001 to 49% by weight, more preferably 0.01 to 10% by weight, still more preferably 0.01 to 5% by weight, and particularly preferably 0.01 to 3% by weight, each based on the total weight of the solid component. Within the above ranges, the reduction of resolution and the deterioration of pattern profiles and dimension accuracy are prevented. In addition, the upper profile of pattern can be made proper even if the time delay between the irradiation of electron beam and the heating after irradiation is prolonged. If the blending amount is 10% by weight or less, the reduction of sensitivity and developability of unexposed area can be prevented. Using the acid-diffusion controller, the storage stability and resolution of the radiation-sensitive composition can be improved. In addition, the change of line width of resist patterns due to the variation of time delay before and after irradiation can be prevented, thereby to make the process stability extremely excellent.

The composition of the invention may contain other components (F) in an amount not adversely affecting the object of the invention, if necessary. Other components (F) may be at least one additives, such as a dissolution promotor, a solubility controller, a sensitizer, a surfactant, an organic carboxylic acid, an phosphorus-containing oxoacid, and a derivative thereof.

(1) Dissolution Promotor

The low molecular weight dissolution promotor is a compound for adequately increasing the dissolving speed of the cyclic compound of formula (1) in a developing solution, such as alkalis, by increasing the solubility, if the solubility is excessively low, and can be used in an amount not adversely affecting the effects of the invention. Examples of the dissolution promotor include a low-molecular weight phenol, such as bisphenols and tris(hydroxyphenyl) methane. The dissolution promotor may be used singly or in combination of two or more. The blending amount of the dissolution promotor varies depending upon the kind of the r cyclic compound to be used, and is preferably 0 to 49% by weight, more preferably 0 to 5% by weight, still more preferably 0 to 1% by weight, and particularly preferably zero, each based on the total weight of the solid component.

(2) Solubility Controller

The solubility controller is a compound for adequately reducing the dissolving speed of the cyclic compound of formula (1) in a developing solution, such as alkalis, by lowering the solubility, if the solubility is excessively high. It is preferred for the solubility controller to cause no chemical change in the steps of baking of resist film, irradiation of radiation and development.

Examples of the solubility controller include aromatic hydrocarbons such as naphthalene, phenanthrene, anthracene and acenaphthene; ketones such as acetophenone, benzophenone and phenyl naphthyl ketone; and sulfones such as methyl phenyl sulfone, diphenyl sulfone and dinaphthyl sulfone. The solubility controllers may be used singly or in combination of two or more.

The blending amount of the solubility controller varies depending upon the kind of the cyclic compound to be used, and is preferably 0 to 49% by weight, more preferably 0 to 5% by weight, still more preferably 0 to 1% by weight, and particularly preferably zero, each based on the total weight of the solid component.

(3) Sensitizer

The sensitizer is a compound for increasing the generation of acid by absorbing the energy of irradiated radiation and transferring the absorbed energy to the acid generator (C), thereby enhancing the apparent sensitivity of the resist. Examples of the sensitizer include, but not limited to, benzophenones, biacetyls, pyrenes, phenothiazines, and fluorenes.

The sensitizer may be used singly or in combination of two or more. The blending amount of the dissolution promotor varies depending upon the kind of the cyclic compound to be used, and is preferably 0 to 49% by weight, more preferably 0 to 5% by weight, still more preferably 0 to 1% by weight, and particularly preferably zero, each based on the total amount of the solid component.

(4) Surfactant

The surfactant is a compound for improving the coating properties and striation of the radiation-sensitive composition and the developability of the resist, etc. The surfactant may be any of anionic, cationic, nonionic and ampholytic, with nonionic surfactants being preferred because they are more effective due to a good affinity to solvents to be used for the production of the radiation-sensitive composition. Examples of the nonionic surfactant include, but not limited to, polyoxyethylene higher alkyl ethers, polyoxyethylene higher alkyl phenyl ethers, and higher fatty acid diesters of polyethylene glycol, which are commercially available under the tradenames: "EFTOP" of Jemco Inc.; "MEGAFACE" of Dai-Nippon Ink & Chemicals, Inc.; "FLUORAD" of Sumitomo 3M Ltd.; "ASAHIGUARD" and "SURFLON" of Asahi Glass Co., Ltd.; "PEPOL" of Toho Chemical Industry Co., Ltd.; "KP" of Shin-Etsu Chemical Co., Ltd.; and "POLYFLOW" of Kyoeisha Chemical Co., Ltd.

The blending amount of the surfactant varies depending upon the kind of the cyclic compound to be used, and is preferably 0 to 49% by weight, more preferably 0 to 5% by weight, still more preferably 0 to 1% by weight, and particularly preferably zero, each based on the total weight of the solid component.

(5) Organic Carboxylic Acid, Phosphorus-containing Oxoacid, Derivative Thereof

The radiation-sensitive composition of the invention may optionally contain an organic carboxylic acid, phosphorus-containing oxoacid, or a derivative thereof in view of preventing the deterioration of sensitivity and improving the resist pattern profile and the stability between a production step and the next production step. These compounds may be used in combination with the acid-diffusion controller or used alone. Preferred examples of the organic carboxylic acid include malonic acid, citric acid, malic acid, succinic acid, benzoic acid, and salicylic acid. Preferred examples of the phosphorus-containing oxoacid and its derivative include phosphoric acid and its derivative, such as ester, for example, phosphoric acid, di-n-butyl phosphate, and diphenyl phosphate; phosphonic acid and its derivative, such as ester, for example, phosphonic acid, dimethyl phosphonate, di-n-butyl phosphonate, phenylphosphonic acid, diphenyl phosphonate, and dibenzyl phosphonate; and phosphinic acid and its derivative, such as ester, for example, phosphinic acid and phenyl phosphinate, with phosphonic acid being particularly preferred.

The organic carboxylic acid, phosphorus-containing oxoacid, and derivative thereof may be used alone or in combination of two or more. The blending amount of these compounds depends on the kind of the cyclic compound to be used and preferably 0 to 49% by weight, more preferably 0 to 5% by weight, still more preferably 0 to 1% by weight, and particularly preferably zero, each based on the total weight of the solid component.

(6) Additives other than Solubility Controller, Sensitizer, Surfactant, and Organic Carboxylic Acid or Phosphorus-containing Oxoacid and Derivative Thereof In addition to the solubility controller, sensitizer, and surfactant, the radiation-sensitive composition of the present invention may contain, if necessary, one or more other additives, as long as the object of the present invention is adversely affected. Such additives include, for example, a dye, pigment and adhesive aid. The dye or pigment visualizes the latent images of exposed portions, thereby reducing adverse influence of halation during the exposing operation. The adhesive aid improves the adhesion to substrates. Other additives may include a halation inhibitor, storage stabilizer, defoaming agent, shape modifier, and specifically 4-hydroxy-4'-methylchalcone.

The total amount of other components (F) is preferably 0 to 49% by weight, more preferably 0 to 5% by weight, still more preferably 0 to 1% by weight, and particularly preferably zero, each based on the total weight of the solid component.

The blending proportions of the radiation-sensitive composition (cyclic compound/acid generator (C)/acid crosslinking agent (G)/acid-diffusion controller (E)/other components (F)) expressed by percent by weight based on the solid component are preferably 50 to 99.4/0.001 to 49/0.5 to 49/0.001 to 49/0 to 49, more preferably 55 to 90/1 to 40/0.5 to 40/0.01 to 10/0 to 5, still more preferably 60 to 80/3 to 30/1 to 30/0.01 to 5/0 to 1, and particularly preferably 60 to 70/10 to 25/2 to 20/0.01 to 3/0.

The blending proportion of each component is selected from the above ranges so that the blending proportions of the components total to 100% by weight. With the above blending proportions, properties, such as the sensitivity, the resolution, and the alkali developability, are good.

The radiation-sensitive composition of the invention is prepared generally just before its use by dissolving each component in a solvent to form a uniform solution and, if necessary, filtering the solution through a filter with about 0.2 μm pore size.

Examples of the solvent to be used in the preparation of the radiation-sensitive composition include, but not limited to, ethylene glycol monoalkyl ether acetates, such as ethylene glycol monomethyl ether acetate, ethylene glycol monoethyl ether acetate, ethylene glycol mono-n-propyl ether acetate, and ethylene glycol mono-n-butyl ether acetate; ethylene glycol monoalkyl ethers, such as ethylene glycol monomethyl ether and ethylene glycol monoethyl ether; propylene glycol monoalkyl ether acetates, such as propylene glycol monomethyl ether acetate, propylene glycol monoethyl ether acetate, propylene glycol mono-n-propyl ether acetate, and propylene glycol mono-n-butyl ether acetate; propylene glycol monoalkyl ethers, such as propylene glycol monomethyl ether and propylene glycol monoethyl ether; lactic esters, such as methyl lactate, ethyl lactate, n-propyl lactate, n-butyl lactate, and n-amyl lactate; esters of aliphatic carboxylic acids, such as methyl acetate, ethyl acetate, n-propyl acetate, n-butyl acetate, n-amyl acetate, n-hexyl acetate, methyl propionate, and ethyl propionate; other esters, such as methyl 3-methoxy propionate, 3-methoxyethyl propionate, methyl 3-ethoxy propionate, 3-ethoxyethyl propionate, methyl 3-methoxy-2-methyl propionate, 3-methoxybutyl acetate, 3-methyl-3-methoxybutyl acetate, butyl 3-methoxy-3-methyl propionate, butyl 3-methoxy-3-methyl lactate, methyl acetacetate, methyl pyruvate, and ethyl pyruvate; aromatic hydrocarbons, such as toluene and xylene; ketones, such as 2-heptanone, 3-heptanone, 4-heptanone, and cyclohexanone; amides, such as N,N-dimethylformamide, N-methylacetamide, N,N-dimethylacetamide, and N-methylpyrrolidone; and lactones, such as γ-lactone. These solvents may be used alone or in combination of two or more.

The radiation-sensitive composition of the invention may contain a resin soluble in an aqueous alkali solution, as long as the object of the present invention is not adversely affected. Examples of the resin soluble in an aqueous alkali solution include novolak resins, polyvinylphenols, polyacrylic acids, polyvinyl alcohols, styrene-maleic anhydride resins, polymers having the units derived from acrylic acid, vinyl alcohol, or vinylphenol, and derivatives thereof. The blending amount of the resin soluble in an aqueous alkali solution varies depending upon the kind of the cyclic compound of formula (1) to be used, and is preferably 30 part by weight or less, more preferably 10 part by weight or less, still more preferably 5 part by weight or less, and particularly preferably zero, each based on 100 part by weight of the cyclic compound.

Formation of Resist Pattern

The present invention also relates to a method of forming resist pattern, which comprises a step of coating the radiation-sensitive composition of the invention on a substrate, thereby forming a resist film; a step of exposing the resist film to radiation; and a step of developing the resist film, thereby forming the resist pattern. The resist pattern of the invention may be an upper layer resist in the multilayer process.

In the formation of a resist pattern, the resist composition of the invention is first applied on a known substrate by a coating method, such as spin coating, cast coating and roll coating, to form a resist film. The substrate is not particularly limited, and a substrate for use in the production of electronic parts with or without patterned wiring, etc. is usable. Specific examples thereof include a silicon wafer, a substrate made of metal, such as copper, chromium, iron, and aluminum, and a glass substrate. The material of the patterned wiring is copper, aluminum, nickel, gold, etc. An inorganic and/or organic coating may be formed on the substrate, if necessary. The inorganic coating include an inorganic anti-reflective coating (inorganic BARC), and the organic coating include an organic anti-reflective coating (organic BARC). The surface of the substrate may be treated with a surface treating agent, such as hexamethylenedisilazane.

Then, the coated substrate is heated, if necessary. The heating temperature varies according to the blending ratio of each component in the radiation-sensitive composition, and preferably 20 to 250° C. and more preferably 20 to 150° C. The adhesion of the resist to the substrate is preferably improved in some cases by the heating. Then, the resist film is exposed in a desired pattern to a radiation selected from the group consisting of visible light, ultraviolet ray, excimer laser, electron beam, extreme ultraviolet ray (EUV), X-ray, and ion beam. The exposing conditions can be suitably selected according to the blending ratio of each component in the radiation-sensitive composition. In the present invention, it is preferred to conduct a heat treatment after the irradiation of radiation to stably form highly accurate fine patterns by the exposure. The heating temperature is preferably 20 to 250° C. and more preferably 20 to 150° C., although depending upon the blending ratio of each component in the radiation sensitive composition.

Then, the exposed resist film is developed with an alkali developing solution to form desired resist patterns. As the alkali developing solution, there may be used an aqueous alkaline solution dissolving, for example, at least one alkaline compound selected from mono-, di- or trialkylamines, mono-, di- or trialkanolamines, heterocyclic amines, tetramethylammonium hydroxide (TMAH) and choline in a concentration of preferably 1 to 10% by mass and more preferably 1 to 5% by mass. The dissolution of the exposed portion in the developing solution is preferably prevented if the concentration is 10% by mass or less.

The alkali developing solution may contain an appropriate amount of an alcohol, such as methanol, ethanol and isopropyl alcohol, or a surfactant mentioned above, with the addition of isopropyl alcohol in 10 to 30% by mass being particularly preferred, because the wetting between the resist and the developing solution is enhanced. After developing with such an aqueous alkaline solution, the developed patterns are generally washed with water.

After forming resist patterns, the substrate is etched to obtain a patterned wiring board. The etching may be performed by known methods, such as dry-etching using a plasma gas and wet-etching using an alkali solution, a copper (II) chloride solution, an iron (III) chloride solution, etc.

After forming resist patterns, the substrate may be plated, for example, by copper plating, solder plating, nickel plating or gold plating.

The remaining resist patterns after etching may be stripped off by an organic solvent or an alkaline aqueous solution stronger than the aqueous alkali solution used for the development. Examples of the organic solvent include PGMEA (propylene glycol monomethyl ether acetate), PGME (propylene glycol monomethyl ether) and EL (ethyl lactate). Examples of the strong alkaline aqueous solution include a 1 to 20% by mass aqueous sodium hydroxide solution and 1 to 20% by mass aqueous potassium hydroxide solution. The stripping of the resist patterns may be performed by dipping method, spray method, etc. The wiring board having the resist patterns thereon may be a multi-layered wiring board and may be formed with small through-holes.

The wiring board may be produced by a lift-off method in which a metal is vacuum-deposited after the formation of resist patterns and then the remaining resist patterns are removed by dissolution into a solution.

EXAMPLES

The present invention will be described in more detail with reference to the following examples. However, it should be noted that the following examples are only illustrative and do not limit the scope of the present invention thereto. In the following synthesis examples, the structure of each compound was identified by $^1$H-NMR measurement.

Synthesis 1

Synthesis of CR-1A (Cyclic Compound (A))

Into a four-necked flask (1000 L) equipped with a dropping funnel thoroughly dried and purged with nitrogen, a Dimroth condenser, a thermometer and a stirring blade, resorcinol (22 g, 0.2 mol) manufactured by Kanto Chemical Co., Inc., 4-isopropylbenzaldehyde (29.6 g, 0.2 mol), and absolute ethanol (200 mL) were charged under nitrogen stream, to prepare an ethanol solution. The solution was heated to 85° C. on a mantle heater under stirring. Then, the solution was added with 75 mL of concentrated hydrochloric acid (35%) dropwise from the dropping funnel over 30 min and further stirred at 85° C. for 3 h. After the reaction, the reaction product was allowed to cool to room temperature and then cooled on an ice bath. After allowing to stand for one hour, pale yellow crude crystals were formed, which were collected by filtration. The crude crystals were washed twice in 500 mL of methanol, collected by filtration, and vacuum dried, to obtain 45.6 g of a compound. The LC-MS analysis showed that the obtained compound had a molecular weight of 960 which was the same as that of the aimed compound. The chemical sifts (δ ppm, TMS standard) of the obtained compound measured by $^1$H-NMR in heavy dimethyl sulfoxide solvent were 1.1 to 1.2 (m, 24H), 2.6 to 2.7 (m, 4H), 5.5 (s, 4H), 6.0 to 6.8 (m, 24H), and 8.4 to 8.5 (d, 8H). From these results, the obtained compound was identified to the aimed compound (CR-1A). The yield was 95%.

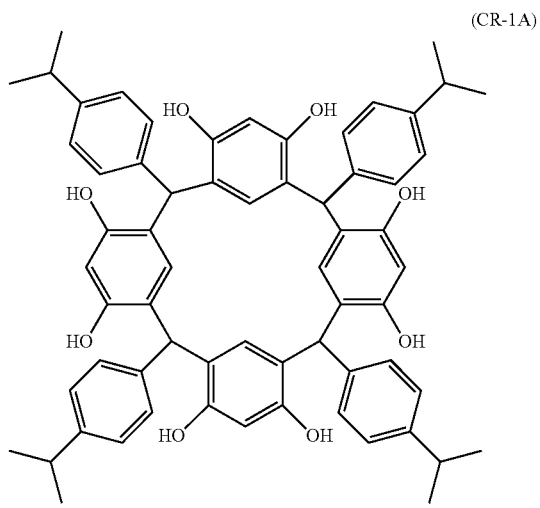 [SMILES: CC(C)c1ccc(C2c3cc(c(O)cc3O)C(c3ccc(C(C)C)cc3)c3cc(c(O)cc3O)C(c3ccc(C(C)C)cc3)c3cc(c(O)cc3O)C(c3ccc(C(C)C)cc3)c3cc2c(O)cc3O)cc1]

(CR-1A)

Synthesis 2

Synthesis of CR-2A (Cyclic Compound (A))

In the same manner as in Synthesis 1 except for using isobutylbenzaldehyde in place of 4-isopropylbenzaldehyde, 49.0 g of a compound was obtained. The LC-MS analysis showed that the obtained compound had a molecular weight of 1017 which was the same as that of the aimed compound. The chemical sifts (δ ppm, TMS standard) of the obtained compound measured by $^1$H-NMR in heavy dimethyl sulfoxide solvent were 1.0 (m, 24H), 2.2 (m, 4H), 2.5 (m, 8H), 5.5 (d, 4H), 5.8 to 6.8 (m, 24H), and 8.4 to 8.6 (t, 8H). From these results, the obtained compound was identified to the aimed compound (CR-2A). The yield was 96%.

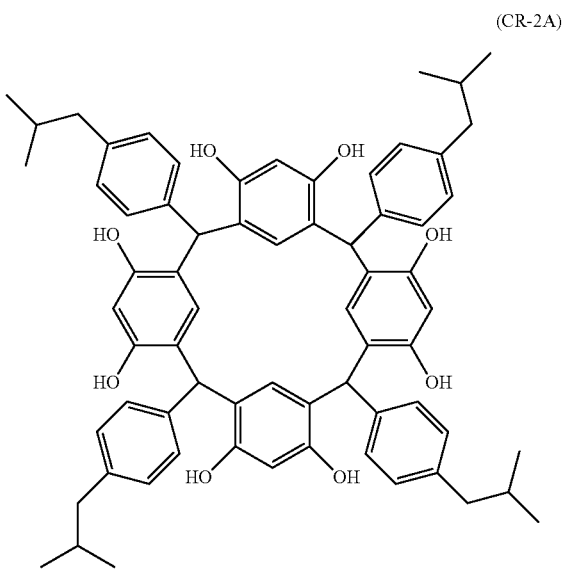 [SMILES: CC(C)Cc1ccc(C2c3cc(c(O)cc3O)C(c3ccc(CC(C)C)cc3)c3cc(c(O)cc3O)C(c3ccc(CC(C)C)cc3)c3cc(c(O)cc3O)C(c3ccc(CC(C)C)cc3)c3cc2c(O)cc3O)cc1]

(CR-2A)

Synthesis 3

Synthesis of CR-3A (Cyclic Compound (A))

In the same manner as in Synthesis 1 except for using biphenylaldehyde in place of 4-isopropylbenzaldehyde, 53.5 g of a compound was obtained. The LC-MS analysis showed that the obtained compound had a molecular weight of 1096 which was the same as that of the aimed compound. The chemical sifts (δ ppm, TMS standard) of the obtained compound measured by $^1$H-NMR in heavy dimethyl sulfoxide solvent were 6.0 to 7.4 (m, 48H) and 8.6 to 8.7 (t, 8H). From these results, the obtained compound was identified to the aimed compound (CR-3A). The yield was 98%.

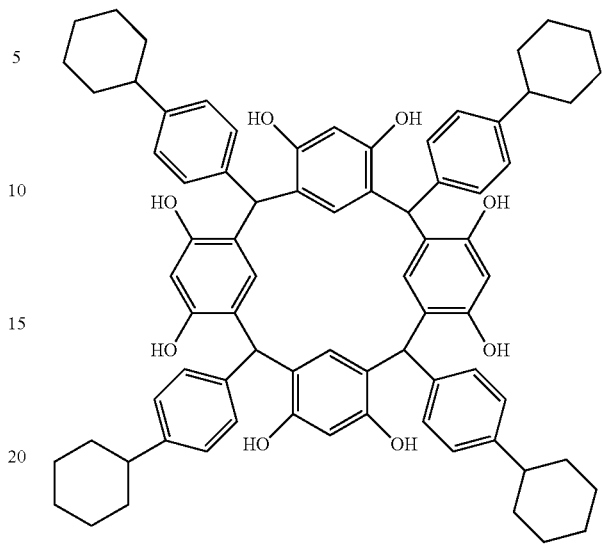

(CR-4A)

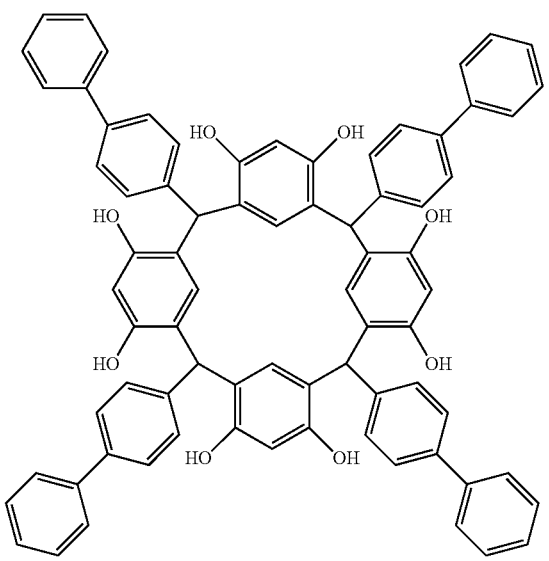

(CR-3A)

Synthesis 4

Synthesis of CR-4A (Cyclic Compound (A))

In the same manner as in Synthesis 1 except for using 4-cyclohexylbenzaldehyde (46.0 g, 0.2 mol) in place of 4-isopropylbenzaldehyde, 50 g of a compound was obtained. The LC-MS analysis showed that the obtained compound had a molecular weight of 1121 which was the same as that of the aimed compound. The chemical sifts (δ ppm, TMS standard) of the obtained compound measured by $^1$H-NMR in heavy dimethyl sulfoxide solvent were 0.8 to 1.9 (m, 44H), 5.5 to 5.6 (d, 4H), 6.0 to 6.8 (m, 24H), and 8.4 to 8.5 (m, 8H). From these results, the obtained compound was identified to the aimed compound (CR-4A). The yield was 91%.

Synthesis Example 1

Synthesis of CR-1 (Cyclic Compound)

In a four-necked flask (1000 L) equipped with a dropping funnel thoroughly dried and purged with nitrogen, a Dimroth condenser, a thermometer and a stirring blade, 3.8 g (40 mmol) of epichlorohydrin was added dropwise to a solution of 9.6 g (10 mmol) of CR-1A synthesized in Synthesis 1 and 4 g (40 mmol) of triethylamine in 300 mL of N-methyl-2-pyrrolidone. The resultant reaction solution was stirred at room temperature for 10 h. After the reaction, the solvent was removed. The obtained solid was purified by column chromatography using a mixed solvent, hexane/ethyl acetate=1/3, to obtain 10.2 g of a compound. The chemical sifts (δ ppm, TMS standard) of the obtained compound measured by $^1$H-NMR in heavy dimethyl sulfoxide solvent were 1.0 (m, 24H), 2.0 to 2.2 (m, 4H), 2.5 (m, 16H), 3.0 (m, 4H), 4.1 (m, 8H), 5.5 (m, 4H), 5.8 to 6.8 (m, 24H), and 8.4 to 8.6 (m, 4H). From these results, the obtained compound was identified to the compound (CR-1) in which 50 mol% of the hydrogen atoms of the phenolic hydroxyl groups in CR-1A was replaced by glycidyl groups.

Synthesis Example 2

Synthesis of CR-2 (Cyclic Compound)

In the same manner as in Synthesis Example 1 except for using CR-2A in place of CR-1A, 10.9 g of a compound was obtained.

The chemical sifts (δ ppm, TMS standard) of the obtained compound measured by $^1$H-NMR in heavy dimethyl sulfoxide solvent were 1.0 (m, 24H), 2.1 to 2.2 (m, 4H), 2.5 (m, 16H), 3.0 (m, 4H), 4.1 (m, 8H), 5.5 (d, 4H), 5.8 to 6.8 (m, 24H), and 8.4 to 8.6 (m, 4H). From these results, the obtained compound was identified to the compound (CR-2) in which 50 mol % of the hydrogen atoms of the phenolic hydroxyl groups in CR-2A was replaced by glycidyl groups.

Synthesis Example 3

Synthesis of CR-3 (Cyclic Compound)

In the same manner as in Synthesis Example 1 except for using CR-3A in place of CR-1A, 11.0 g of a compound was obtained.

The chemical sifts (δ ppm, TMS standard) of the obtained compound measured by $^1$H-NMR in heavy dimethyl sulfoxide solvent were 2.5 (m, 8H), 3.0 (m, 4H), 4.1 (m, 8H), 6.0 to 7.4 (m, 48H), and 8.6 to 8.7 (m, 4H). From these results, the obtained compound was identified to the compound (CR-3) in which 50 mol % of the hydrogen atoms of the phenolic hydroxyl groups in CR-3A was replaced by glycidyl groups.

Synthesis Example 4

Synthesis of CR-4 (Cyclic Compound)

In the same manner as in Synthesis Example 1 except for using CR-4A in place of CR-1A, 11.0 g of a compound was obtained.

The chemical sifts (δ ppm, TMS standard) of the obtained compound measured by $^1$H-NMR in heavy dimethyl sulfoxide solvent were 0.8 to 1.9 (m, 44H), 2.5 (m, 8H), 3.0 (m, 4H), 4.1 (m, 8H), 5.5, 5.6 (m, 4H), 6.0 to 6.8 (m, 24H), and 8.4 to 8.5 (m, 4H). From these results, the obtained compound was identified to the compound (CR-4) in which 50 mol % of the hydrogen atoms of the phenolic hydroxyl groups in CR-4A was replaced by glycidyl groups.

Synthesis Example 5

Synthesis of CR-5 (Cyclic Compound)

In the same manner as in Synthesis Example 4 except for using 1.9 g (20 mmol) of epichlorohydrin, 9.0 g of a compound was obtained.

The chemical sifts (δ ppm, TMS standard) of the obtained compound measured by $^1$H-NMR in heavy dimethyl sulfoxide solvent were 0.8 to 1.9 (m, 44H), 2.5 (m, 4H), 3.0 (m, 2H), 4.1 (m, 4H), 5.5,5.6 (m, 4H), 6.0 to 6.8 (m, 24H), and 8.4 to 8.5 (m, 6H). From these results, the obtained compound was identified to the compound (CR-5) in which 25 mol% of the hydrogen atoms of the phenolic hydroxyl groups in CR-4A was replaced by glycidyl groups.

Synthesis Example 6

Synthesis of CR-6 (Cyclic Compound)

In the same manner as in Synthesis Example 4 except for using 7.6 g (80 mmol) of epichlorohydrin, 12.0 g of a compound was obtained.

The chemical sifts (δ ppm, TMS standard) of the obtained compound measured by $^1$H-NMR in heavy dimethyl sulfoxide solvent were 0.8 to 1.9 (m, 44H), 2.5 (m, 12H), 3.0 (m, 6H), 4.1 (m, 12H), 5.5, 5.6 (m, 4H), 6.0 to 6.8 (m, 24H), and 8.4 to 8.5 (m, 2H). From these results, the obtained compound was identified to the compound (CR-6) in which 75 mol % of the hydrogen atoms of the phenolic hydroxyl groups in CR-4A was replaced by glycidyl groups.

Examples 1 to 6 and Comparative Examples 1 to 4

(1) Solubility of Compound in Safety Solvent

The compounds obtained in Synthesis Examples 1 to 6 and Synthesis 1 to 4 were evaluated for the solubility in propylene glycol monomethyl ether (PGME) and cyclohexanone (CHN). The results are shown in Table 1.

A: 4.0 wt %≤amount
B: 1.0 wt %≤dissolved amount<4.0 wt %
C: dissolved amount<1.0 wt %

TABLE 1

|  | Compound | PGME | CHN |
| --- | --- | --- | --- |
| Example 1 | CR-1 | A | A |
| Example 2 | CR-2 | A | A |
| Example 3 | CR-3 | A | A |
| Example 4 | CR-4 | A | A |
| Example 5 | CR-5 | A | A |
| Example 6 | CR-6 | A | A |
| Comparative Example 1 | CR-1A | B | A |
| Comparative Example 2 | CR-2A | C | B |
| Comparative Example 3 | CR-3A | C | A |
| Comparative Example 4 | CR-4A | B | A |

Examples 7 to 12 and Comparative Examples to 8

(2) Patterning Test

A homogeneous solution of the components shown in Table 2 was filtered through a Teflon (trademark) membrane filter having a pore size of 0.1 μm to prepare each radiation-sensitive composition. Each radiation-sensitive composition was evaluated for the following properties. The results are shown in Table 3.

(2-1) Evaluation of Resolution

After applying the resist onto a clean silicon wafer by a spin coating method, the applied resist was subjected to pre-exposure baking (PB) in an oven at 110° C. to form a resist film having a thickness of 60 nm. The resist film was irradiated with electron beam set at a 1:1 line-and-space with 50 nm intervals using an electron beam lithography system (ELS-7500 manufactured by Elionix Co., Ltd.). After irradiation, each resist film was heated for 90 s at predetermined temperature and developed by immersing in a 2.38% by weight aqueous solution of TMAH for 60 s, and thereafter, rinsed with water for 30 s and dried, to form a negative-type resist pattern. The obtained line-and-space pattern was observed under a scanning electron microscope (S-4800 manufactured by Hitachi High-Technologies Corporation). The dose amount ($\mu C/cm^2$) for the observation was employed as the sensitivity. The results are shown in Table 3.

(2-2) Evaluation of Pattern Profile

The evaluation was made by observing the cross-sectional photograph of the obtained 1:1 line-and-space with 50 nm intervals under a scanning electron microscope (S-4800 manufactured by Hitachi High-Technologies Corporation). The results are shown in Table 3.

A: rectangular pattern (good pattern)
B: nearly rectangular pattern (nearly good pattern)
C: not rectangular pattern (not good pattern)

(2-3) Evaluation of Line Edge Roughness (LER)

The distance between the edge and the base line was measured at 300 points which were randomly selected along the lengthwise direction (0.75 μm) of the 1:1 line-and-space with 50 nm intervals. The measurement was conducted using Hitachi Semiconductor SEM, terminal PC and V5 off-line measuring software (available from Hitachi Science Systems, Ltd.). From the measured results, the standard deviation (3σ) was calculated. The results are shown in Table 3.

A: LER (3σ)≤3.5 nm (good LER)

C: 3.5 nm<LER (3σ) (not good LER)

TABLE 2

| | Compound (g) | Acid generator (C) (g) | Acid crosslinking agent (G) (g) | Acid-diffusion controller (E) (g) | Solvent (g) |
|---|---|---|---|---|---|
| Example 7 | CR-4 1.0 | P-1 0.3 | C-1 0.3 | Q-1 0.03 | S-1 30.0 |
| Example 8 | CR-4 1.0 | P-2 0.3 | C-1 0.3 | Q-1 0.03 | S-1 30.0 |
| Example 9 | CR-4 1.0 | P-1 0.3 | C-2 0.3 | Q-1 0.03 | S-1 30.0 |
| Example 10 | CR-5 1.0 | P-1 0.3 | C-1 0.3 | Q-1 0.03 | S-1 30.0 |
| Example 11 | CR-6 1.0 | P-1 0.3 | C-1 0.3 | Q-1 0.03 | S-1 30.0 |
| Example 12 | CR-1 1.0 | P-1 0.3 | C-1 0.3 | Q-1 0.03 | S-1 30.0 |
| Comparative Example 5 | CR-4A 1.0 | P-1 0.3 | C-1 0.3 | Q-1 0.03 | S-1 30.0 |
| Comparative Example 6 | CR-4A 1.0 | P-2 0.3 | C-1 0.3 | Q-1 0.03 | S-1 30.0 |
| Comparative Example 7 | CR-4A 1.0 | P-1 0.3 | C-2 0.3 | Q-1 0.03 | S-1 30.0 |
| Comparative Example 8 | CR-1A 1.0 | P-1 0.3 | C-1 0.3 | Q-1 0.03 | S-1 30.0 |

Acid generator (C)
P-1: Triphenylbenzenesulfonium nonafluorobutane sulfonate (Midori Kagaku Co., Ltd.)
P-2: Triphenylbenzenesulfonium trifluoromethane sulfonate (Midori Kagaku Co., Ltd.)
Aid crosslinking agent (G)
C-1: Nikalac MW-100LM (Sanwa Chemical Co., Ltd.)
C-2: Nikalac MX-270 (Sanwa Chemical Co., Ltd.)
Acid-diffusion controller (E)
Q-1: trioctylamine (Tokyo Kasei Kogyo Co., Ltd.)
Solvent
S-1: propylene glycol monomethyl ether (Tokyo Kasei Kogyo Co., Ltd.)

TABLE 3

| | PEB (° C.) | Sensitivity (μC/cm$^2$) | Pattern profile | LER (3σ) |
|---|---|---|---|---|
| Example 7 | 110 | 25.0 | A | A |
| Example 8 | 110 | 25.0 | B | A |
| Example 9 | 110 | 25.0 | A | A |
| Example 10 | 110 | 30.0 | A | A |
| Example 11 | 110 | 20.0 | A | A |
| Example 12 | 110 | 70.0 | A | A |
| Comparative Example 5 | 110 | 30.0 | A | A |
| Comparative Example 6 | 110 | 30.0 | B | A |
| Comparative Example 7 | 110 | 30.0 | A | A |
| Comparative Example 8 | 110 | 80.0 | A | A |

PEB: heating temperature after electron beam irradiation.

As described above, the composition containing the compound of the invention is highly sensitivity and capable of forming a resist pattern with good profile as compared with a composition containing a comparative compound. The compounds of the invention other than those described above also exhibit similar effect as long as satisfying the requirements of the invention described above.

Industrial Applicability

The cyclic compound of the invention is useful as an acid-amplified, non-polymeric resist material and suitably used as a component of a radiation-sensitive composition for forming a resist pattern.

What is claimed is:

1. A cyclic compound represented by formula (1):

(1)

wherein each L is independently a single bond or a divalent organic group selected from the group consisting of a linear or branched alkylene group having 1 to 20 carbon atoms, a cycloalkylene group having 3 to 20 carbon atoms, an arylene group having 6 to 24 carbon atoms, —O—, —OC(═O)—, —OC(═O)—O—, —N(R$^5$)—C(═O)— wherein R$^5$ is hydrogen or an alkyl group having 1 to 10 carbon atoms, —N(R$^5$)—C(═O)O— wherein R$^5$ is as defined above, —S—, —SO—, —SO$_2$—, and a combination of any of preceding groups;

each R$^1$ is independently an alkyl group having 1 to 20 carbon atoms, a cycloalkyl group having 3 to 20 carbon atoms, an aryl group having 6 to 20 carbon atoms, an alkoxyl group having 1 to 20 carbon atoms, cyano group, nitro group, hydroxyl group, a heterocyclic group, a halogen, carboxyl group, glycidyl group, an alkylsilyl group having 1 to 20 carbon atoms, or hydrogen atom, with the proviso that at least one of R$^1$ is glycidyl group and another at least one of R$^1$ is hydrogen atom;

each R' is independently an aryl group represented by the following formula:

wherein R$^4$ is a cycloalkyl group having 3 to 20 carbon atoms, an aryl group having 6 to 20 carbon atoms, an alkoxy group having 1 to 20 carbon atoms, cyano group, nitro group, a heterocyclic group, carboxyl group, hydroxyl group, glycidyl group, or an alkylsilyl group having 1 to 20 carbon atoms, and p is an integer of 1 to 5; and each m is an integer of 1 to 4.

2. The cyclic compound according to claim 1, represented by formula (2):

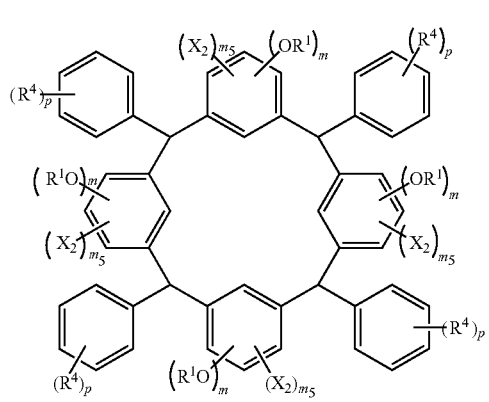

(2)

wherein $R^1$, $R^4$, p, and m are as defined above, $X_2$ is a hydrogen or halogen atom, $m_5$ is an integer of 0 to 3, and $m+m_5=4$.

3. The cyclic compound according to claim 1, having a molecular weight of 800 to 5000.

4. A method of producing the cyclic compound according to claim 1, which comprises subjecting at least one aldehyde compound (A1) and at least one phenol compound (A2) to condensation reaction, to obtain a cyclic compound (A); and subjecting the cyclic compound (A) and at least one epihalohydrin (A3) to dehydrohalogenation reaction.

5. The method according to claim 4, wherein the aldehyde compound (A1) has 1 to 4 formyl groups and 2 to 59 carbon atoms, and the phenol compound (A2) has 1 to 3 phenolic hydroxyl groups and 6 to 15 carbon atoms.

6. The method according to claim 4, wherein the cyclic compound (A) has a molecular weight of 700 to 5000.

7. The method according to claim 4, wherein by the dehydrohalogenation reaction between the cyclic compound (A) and the at least one epihalohydrin (A3), at least one phenolic hydroxyl group of the cyclic compound (A) is converted to glycidyloxy group while maintaining another at least one phenolic hydroxyl group unchanged.

8. A radiation-sensitive composition comprising the cyclic compound according to claim 1 and a solvent.

9. The radiation-sensitive composition according to claim 8, comprising 1 to 80% by weight of a solid component and 20 to 99% by weight of a solvent.

10. The radiation-sensitive composition according to claim 9, wherein a content of the cyclic compound is 50 to 99.999% by weight of a total weight of the solid component.

11. The radiation-sensitive composition according to claim 8, further comprising an acid generator (C) which directly or indirectly generates acid upon exposure to any radiation selected from the group consisting of visible light, ultraviolet ray, excimer laser, electron beam, extreme ultraviolet ray (EUV), X-ray, and ion beam.

12. The radiation-sensitive composition according to claim 8, further comprising an acid crosslinking agent (G).

13. The radiation-sensitive composition according to claim 8, further comprising an acid-diffusion controller (E).

14. The radiation-sensitive composition according to claim 8, wherein the cyclic compound is represented by formula (2):

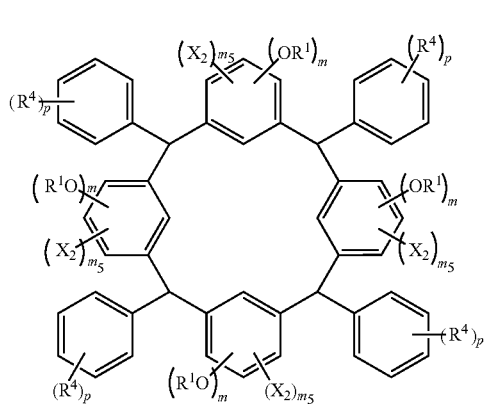

(2)

wherein $R^1$, $R^4$, p, and m are as defined above, $X_2$ is a hydrogen or halogen atom, $m_5$ is an integer of 0 to 3, and $m+m_5=4$.

15. The radiation-sensitive composition according to claim 8, wherein the cyclic compound is selected from the group consisting of compounds represented by formulae (6-5) to (6-8):

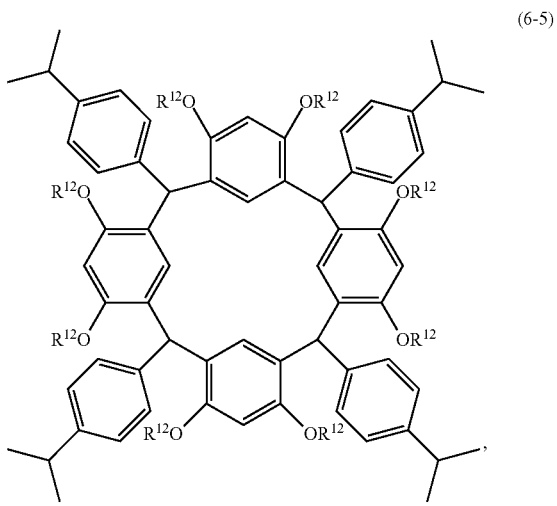

(6-5)

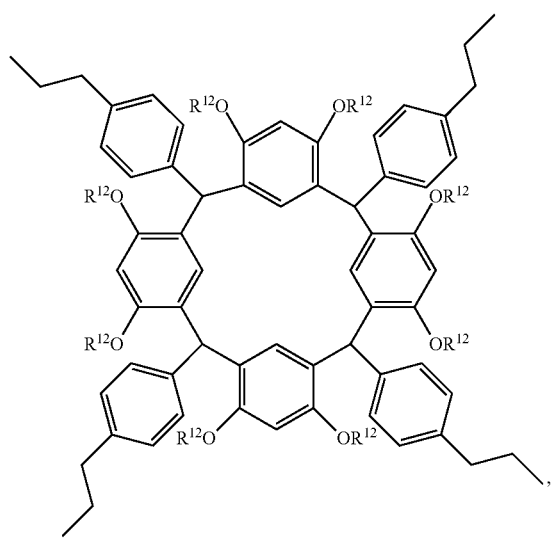

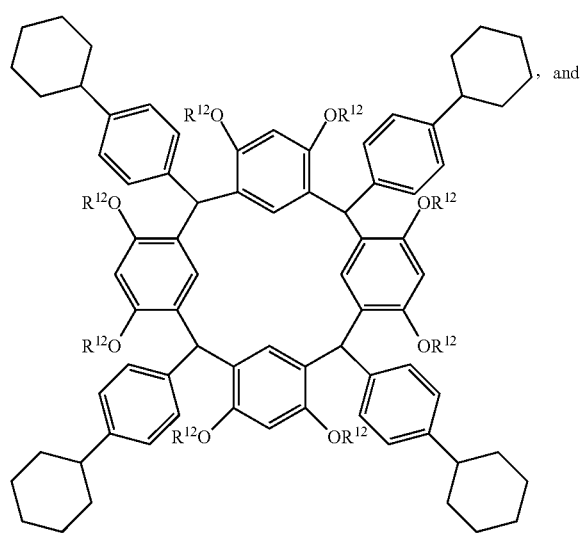

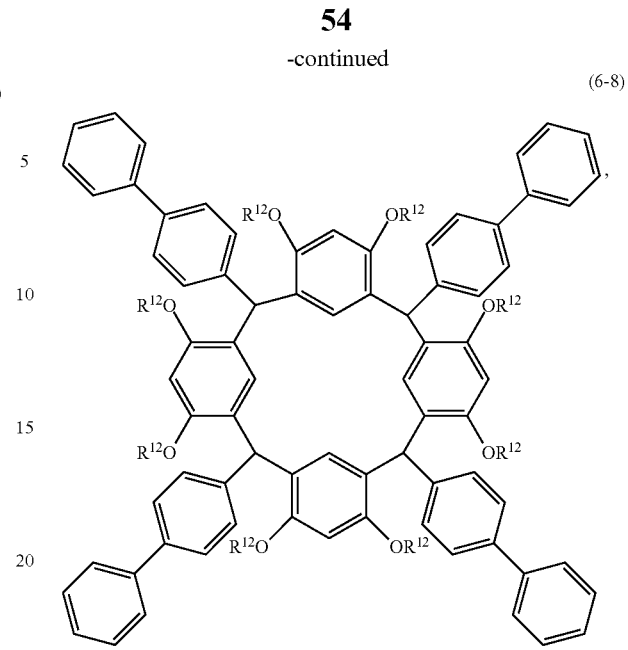

wherein $R^{12}$ is glycidyl group or hydrogen atom, with the proviso that at least one $R^{12}$ is glycidyl group and another at least one of $R^{12}$ is hydrogen atom.

16. The radiation-sensitive composition according to claim 9, wherein the solid component comprises 50 to 99.4% by weight of the cyclic compound, 0.001 to 49% by weight of the acid generator (C), 0.5 to 49% by weight of the acid crosslinking agent (G), 0.001 to 49% by weight of the acid-diffusion controller (E), and 0 to 49% by weight of an optional component (F), each based on the solid component.

17. The radiation-sensitive composition according to claim 8, capable of forming an amorphous film by spin coating.

18. The radiation-sensitive composition according to claim 17, wherein a dissolving speed of the amorphous film into a 2.38% by weight aqueous solution of tetramethylammonium hydroxide at 23° C. is 10 Å/s or more.

19. A method of forming resist pattern, which comprises a step of coating the radiation-sensitive composition according to claim 8 on a substrate, thereby forming a resist film; a step of exposing the resist film to radiation; and a step of developing the exposed resist film.

20. A resist material comprising the compound of claim 1.

* * * * *